(12) United States Patent
Hayashi et al.

(10) Patent No.: US 7,700,792 B2
(45) Date of Patent: Apr. 20, 2010

(54) HIGHLY ACTIVE LYSOPHOSPHATIDIC ACID AND METHOD OF SCREENING THEREWITH

(75) Inventors: Akio Hayashi, Tsukuba (JP); Shinji Nakade, Tsukuba (JP); Hidehiro Suzuki, Tsukuba (JP)

(73) Assignee: Ono Pharmaceutical Co., Ltd., Osaka-shi, Osaka (JP)

( * ) Notice: Subject to any disclaimer, the term of this patent is extended or adjusted under 35 U.S.C. 154(b) by 968 days.

(21) Appl. No.: 10/584,283

(22) PCT Filed: Dec. 22, 2004

(86) PCT No.: PCT/JP2004/019241

§ 371 (c)(1),
(2), (4) Date: Jun. 26, 2006

(87) PCT Pub. No.: WO2005/064332

PCT Pub. Date: Jul. 14, 2005

(65) Prior Publication Data

US 2007/0161604 A1    Jul. 12, 2007

(30) Foreign Application Priority Data

Dec. 26, 2003 (JP) ............... 2003-432844
Jul. 30, 2004 (JP) ............... 2004-224351

(51) Int. Cl.
*C07F 9/02* (2006.01)
(52) U.S. Cl. ............... 554/78; 514/141; 514/143
(58) Field of Classification Search ............... None
See application file for complete search history.

(56) References Cited

U.S. PATENT DOCUMENTS 6,380,177 B1 * 4/2002 Erickson ............... 514/141

FOREIGN PATENT DOCUMENTS

JP      2003-294725 A    10/2003
WO    WO 03/007991 A1    1/2003

OTHER PUBLICATIONS

Koji Bandoh, "Lysophosphatidic acid receptors of the EDG family are differentially activated by LPA species", FEBS Letters, vol. 478, pp. 159 to 165, (Jul. 28, 2000).

* cited by examiner

*Primary Examiner*—Daniel M Sullivan
*Assistant Examiner*—Sudhakar Katakam
(74) *Attorney, Agent, or Firm*—Sughrue Mion, PLLC

(57) ABSTRACT

To provide a highly active LPA and a method of screening therewith.

There is provided a method of screening a preventive and/or therapeutic substance for diseases in which LPA takes part, characterized in that a compound represented by any of formula (I), (II) and (III):

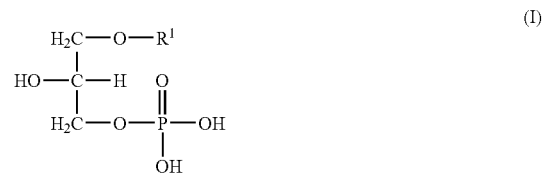

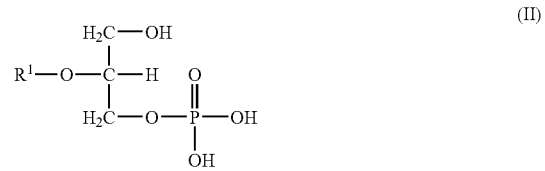

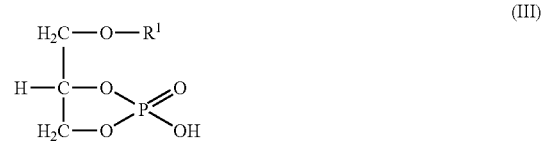

[wherein the meaning of characters are described in the description] is used. The compounds obtained by the screening method or the screening kit of the present invention, their salts, their solvates and prodrugs thereof would modulate the binding of highly active LPA with LPA receptor in human and other mammals, so that they can be used as a preventive and/or therapeutic agent for diseases in which LPA takes part, for example, urinary diseases, central nervous diseases, inflammatory diseases, circulatory diseases, cancer, diabetes, immune system disorders and alimentary diseases.

17 Claims, 1 Drawing Sheet

HIGHLY ACTIVE LYSOPHOSPHATIDIC ACID AND METHOD OF SCREENING THEREWITH

TECHNICAL FIELD

The present invention relates to a new substance "highly active lysophosphatidic acid" (hereinafter referred to as "highly active LPA") and a method of screening a preventive and/or therapeutic substance for diseases in which lysophosphatidic acid (hereinafter referred to as "LPA") takes part, which comprises using the highly active LPA.

Background Art

LPA which is one of the lipid mediators is called generally as lysophospholipid along with sphingosine-1-phosphate. LPA is a ligand of GPCR (G-protein coupled receptor which has seven transmembrane domain) named EDG (Endothelial differentiation gene)-2, -4, or -7, and it is known to be involved in regulation of various cell function or vital function and appearance or progression of various diseases (for example, urinary diseases, central nervous diseases, inflammatory diseases, circulatory diseases, cancer, diabetes, immune system disorders and alimentary diseases) through their binding to receptors.

Because a compound which modulate a binding between LPA and its receptor is able to become a preventive and/or therapeutic drug, the various methods of screening to obtain it are developed (for example, see the specification of WO99/24569 (patent document 1), or WO96/39436 (patent document 2)).

Generally, lipid mediator which functionate as a ligand of GPCR is not or less detectable in blood of healthy body as in the case of PAF (platelet activating factor) or leukotriene. On the other hand, LPA is known to be detectable in blood serum of mammals at a very high concentration of a few μg per mL. When ligand is highly excessive as described, LPA receptor is expected to be always activated. But, in cases where chemically synthesized agonist for LPA receptor is administered to living body, the receptor is activated as well as general response in ligand-receptor reaction. Therefore, LPA receptor is usually inactive in spite of excessive existence of its ligand LPA, and when LPA receptor is activated by various diseases, it is anticipated that the ligand which activates LPA receptor is different from LPA.

[patent document 1] WO99/24569
[patent document 2] WO96/39436

DISCLOSURE OF THE INVENTION

Problems to be Solved by the Invention

The problem to be solved by the present invention is to find a new ligand other than LPA which has functions to activate LPA receptor in living body, and to establish a high-sensitive screening system for a substance which modulates a binding between LPA receptor and its ligand.

Means for Solving the Problems

The present inventors have intensively studied, and as a result, have found that LPA binds to LPA receptor and functions as highly active new ligand after modification such as oxidation in living body. The present inventors have studied more based on this knowledge, and have completed the present invention.

Thus, the present invention relates to:

[1] A method of screening a preventive and/or therapeutic substance for diseases in which LPA takes part, which comprises using an optionally labelled highly active LPA;

[2] The method according to above [1], wherein the highly active LPA is a compound represented by formula (I), (II) or (III):

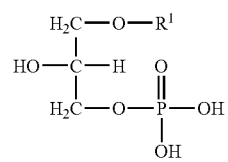
(I)

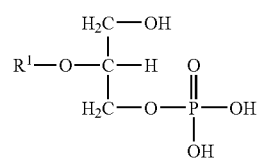
(II)

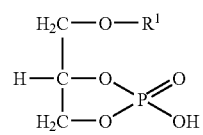
(III)

[wherein $R^1$ represents an aliphatic hydrocarbon group or an aliphatic hydrocarbon-carbonyl group which is oxidized, nitrated, nitrosated, nitrohydrylated and/or aminated, and wherein asymmetric carbon means R-configuration, S-configuration or a mixture thereof in any ratio.],
a salt thereof or a solvate thereof;

[3] The method according to above [2], wherein the number of carbon atom of main chain of $R^1$ is 6 to 26;

[4] The method according to above [2], wherein $R^1$ represents an aliphatic hydrocarbon group or an aliphatic hydrocarbon-carbonyl group which contains one or more part(s) selected from the following group Q as substructure; the group Q represents the group consisting of

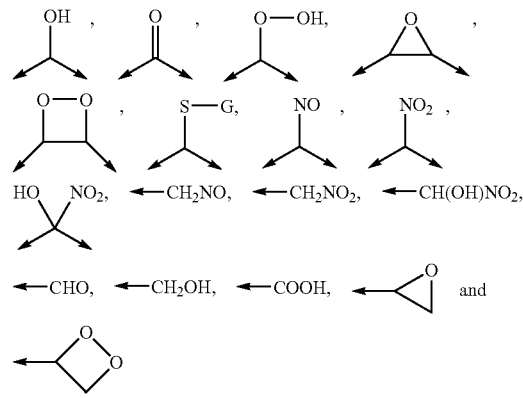

[wherein arrowhead represents a binding site(s); G represents

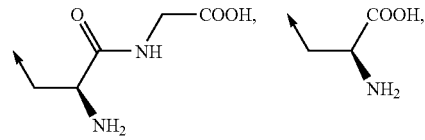

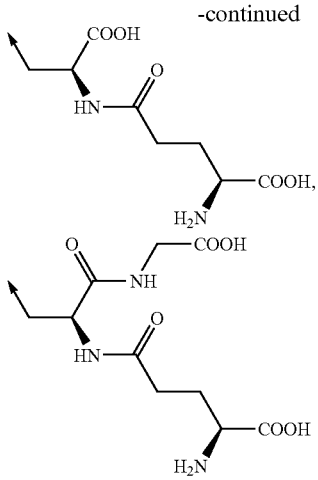

-continued

[wherein arrowhead represents a binding site(s).]
or hydrogen atom, and
wherein asymmetric carbon means R-configuration, S-configuration or a mixture thereof in any ratio.];

[5] The method according to above [4], wherein $R^1$ represents

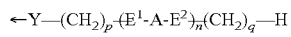

[wherein arrowhead represents a binding site(s); Y represents carbonyl or methylene; p and q each independently represents 0 or an integer of 1 to 7; $E^1$ and $E^2$ each independently represents C1-4 alkylene, C2-4 alkenylene or a bond; A represents a bond,

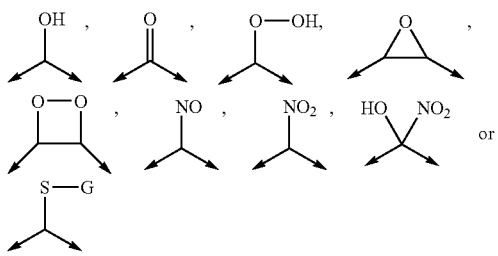

[wherein arrowhead represents a binding site(s); G has the same meaning as in above [4], and wherein asymmetric carbon means R-configuration, S-configuration or a mixture thereof in any ratio.];

n represents an integer of 1 to 6 and when n represents 2 or more, plural $E^1$, plural $E^2$ and plural A are the same or different, and wherein at least one of A in $R^1$ represents

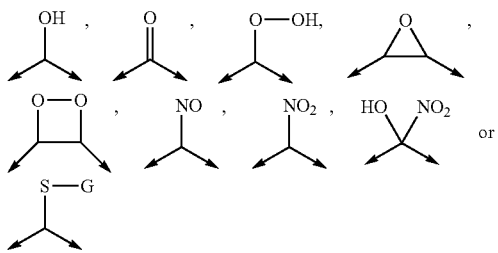

[wherein arrowhead represents a binding site(s); G has the same meaning as in above [4], and wherein asymmetric carbon means R-configuration, S-configuration or a mixture thereof in any ratio.]];

[6] The method according to above [5], wherein $R^1$ represents

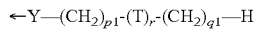

[wherein arrowhead represents a binding site(s); Y represents carbonyl or methylene; p1 and q1 each independently represents an integer of 1 to 7; T represents

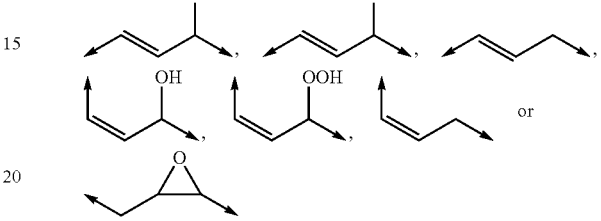

[wherein arrowhead represents a binding site(s), and wherein asymmetric carbon means R-configuration, S-configuration or a mixture thereof in any ratio.];

r represents an integer of 1 to 5 and when r represents 2 or more, plural r are the same or different, and wherein at least one of T in $R^1$ represents

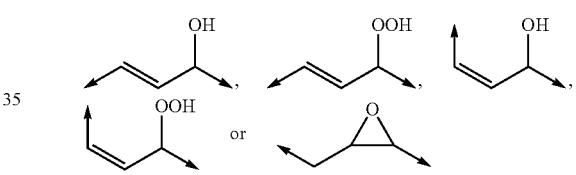

[wherein arrowhead represents a binding site(s), and wherein asymmetric carbon means R-configuration, S-configuration or a mixture thereof in any ratio.)]];

[7] The method according to above [6], wherein $R^1$ represents a C18 aliphatic hydrocarbon-carbonyl group which contains 2 to 3 double bonds and is substituted with 1 hydroperoxy group;

[8] The method according to above [7], wherein $R^1$ represents

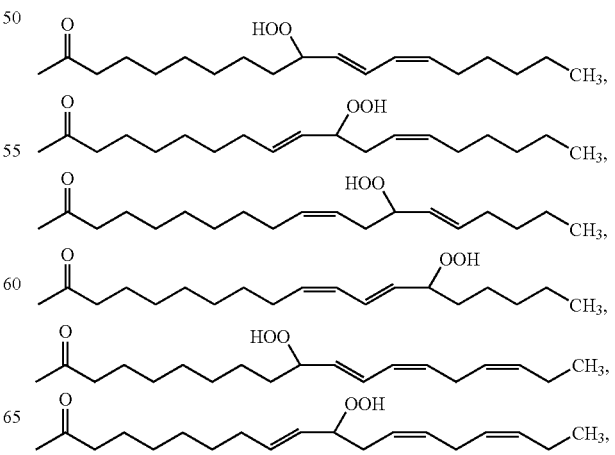

-continued

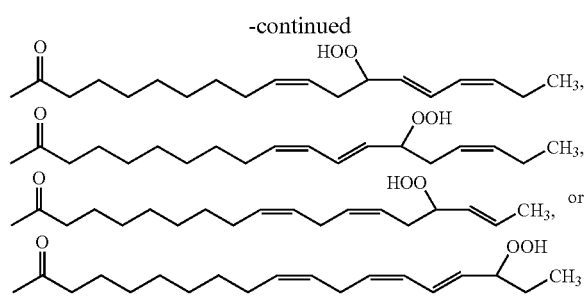

[wherein asymmetric carbon means R-configuration, S-configuration or a mixture thereof in any ratio.];

[9] The method according to above [6], wherein $R^1$ represents a C18 aliphatic hydrocarbon-carbonyl group which contains 0 or 1 to 2 double bond(s) and is substituted with 1 to 3 epoxy group(s);

[10] The method according to above [9], wherein $R^1$ represents

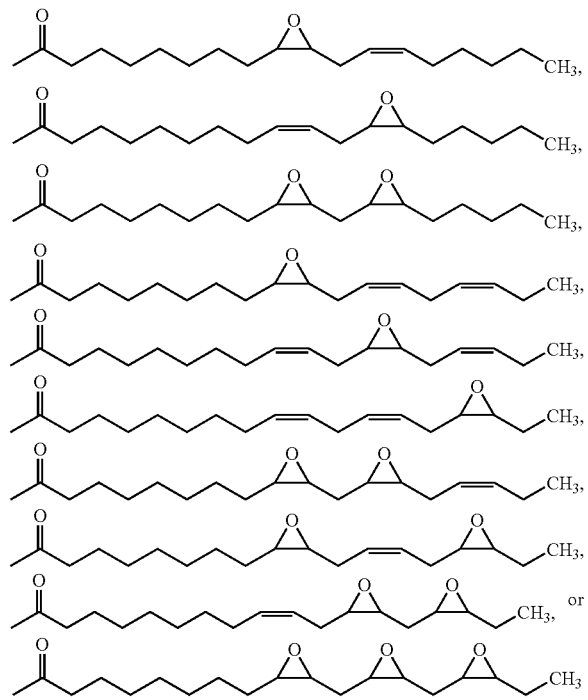

[wherein asymmetric carbon means R-configuration, S-configuration or a mixture thereof in any ratio.];

[11] The method according to above [1], wherein the disease in which LPA takes part is urinary disease, central nervous disease, inflammatory disease, circulatory disease, cancer, diabetes, immune system disorder or alimentary disease;

[12] The method according to above [11], wherein the urinary disease is urinary disturbance;

[13] A screening kit for a preventive and/or therapeutic substance for diseases in which LPA takes part, which comprises using an optionally labelled highly active LPA;

[14] An agent for prevention and/or treatment of urinary disease, central nervous disease, inflammatory disease, circulatory disease, cancer, diabetes, immune system disorder or alimentary disease which comprises the compound, the salt thereof, the solvate thereof or the prodrug thereof obtained by using the method depicted in above [1] and/or the kit depicted in above [13];

[15] The agent according to above [14], which is the agent for prevention and/or treatment of urinary disturbance;

[16] An agent for prevention and/or treatment of urinary disturbance which comprises one or more of selected from the group consisting of α1-antagonist, anticholinergic drug, 5α-reductase inhibitor and antiandrogen drug in combination with the compound, the salt thereof, the solvate thereof or the prodrug thereof obtained by using the method depicted in above [1] and/or the kit depicted in above [13];

[17] The method according to above [1], which comprises using both [1] the optionally labelled highly active LPA and [2] a LPA receptor protein, a partial peptide thereof, or a salt thereof;

[18] The method according to above [17], wherein the LPA receptor is EDG-2, EDG-4, EDG-7 or GPR23;

[19] The method according to above [17], which comprises comparing (1) the measured increase of intracellular concentration of calcium ion of the cell after contacting (a) the optionally labelled highly active LPA and (b) the cell which comprises the LPA receptor protein, to (2) the one after contacting (a) the optionally labelled highly active. LPA, (b) the cell which comprises the LPA receptor protein and (c) the testing compound;

[20] The method according to above [17], which comprises comparing (1) the amount of the labelled highly active LPA which is bound to the LPA receptor protein, the partial peptide thereof, or the salt thereof after contacting (a) the labelled highly active LPA and (b) the LPA receptor protein, the partial peptide thereof, or the salt thereof, to (2) the one after contacting (a) the labelled highly active LPA, (b) the LPA receptor protein, the partial peptide thereof, or the salt thereof and (c) the testing compound;

[21] The method according to above [17], which comprises comparing (1) the amount of the labelled highly active LPA which is bound to the cell after contacting (a) the labelled highly active LPA and (b) the cell which comprises the LPA receptor protein, to (2) the one after contacting (a) the labelled highly active LPA, (b) the cell which comprises the LPA receptor protein and (c) the testing compound;

[22] The method according to above [17], which comprises comparing (1) the amount of the labelled highly active LPA which is bound to the membrane fraction of the cell after contacting (a) the labelled highly active LPA and (b) the membrane fraction of the cell which comprises the LPA receptor, to (2) the one after contacting (a) the labelled highly active LPA, (b) the membrane fraction of the cell which comprises the LPA receptor and (c) the testing compound;

[23] An antibody against highly active LPA;

[24] The antibody according to above [23], which is a neutralizing antibody for inactivating signal transduction of LPA receptor;

[25] A diagnostic product which comprises the antibody depicted in above [23], for diseases in which LPA takes part;

[26] A process for production of a preventive and/or therapeutic substance for diseases in which LPA takes part, which comprises the process of screening a compound using the method of screening depicted in above [17];

[27] A chemically or enzymatically synthesized compound represented by formula (I), (II) or (III):

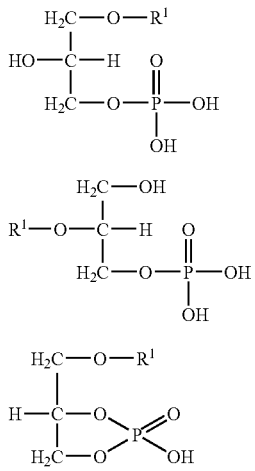

[wherein R¹ represents an aliphatic hydrocarbon group or an aliphatic hydrocarbon-carbonyl group which is oxidized, nitrated, nitrosated, nitrohydrylated and/or aminated, and wherein asymmetric carbon means R-configuration, S-configuration or a mixture thereof in any ratio.],
a salt thereof or a solvate thereof;

[28] The compound according to above [27], wherein R¹ represents a C18 aliphatic hydrocarbon-carbonyl group which contains 2 to 3 double bonds and is substituted with 1 hydroperoxy group;

[29] The compound according to above [28], wherein R¹ represents

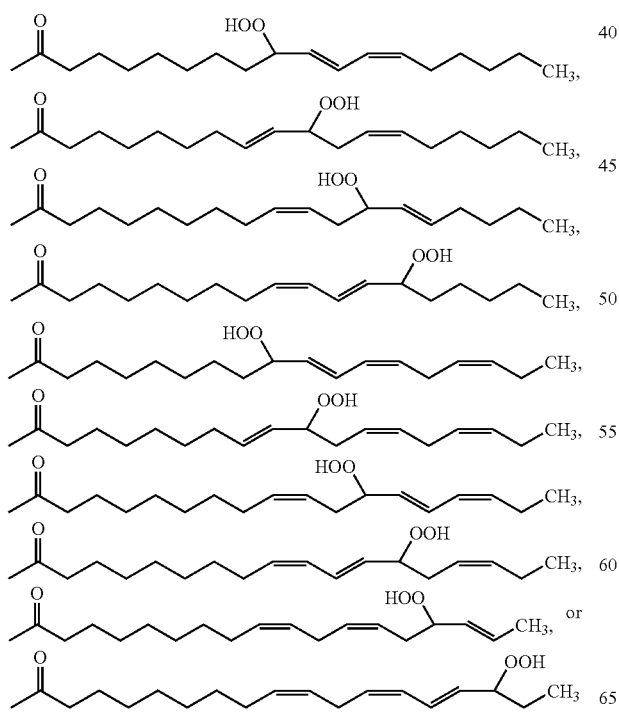

[wherein asymmetric carbon means R-configuration, S-configuration or a mixture thereof in any ratio.];

[30] The compound according to above [27], wherein R¹ represents a C18 aliphatic hydrocarbon-carbonyl group which contains 0 or 1 to 2 double bond(s) and is substituted with 1 to 3 epoxy group(s);

[31] The compound according to above [30], wherein R¹ represents

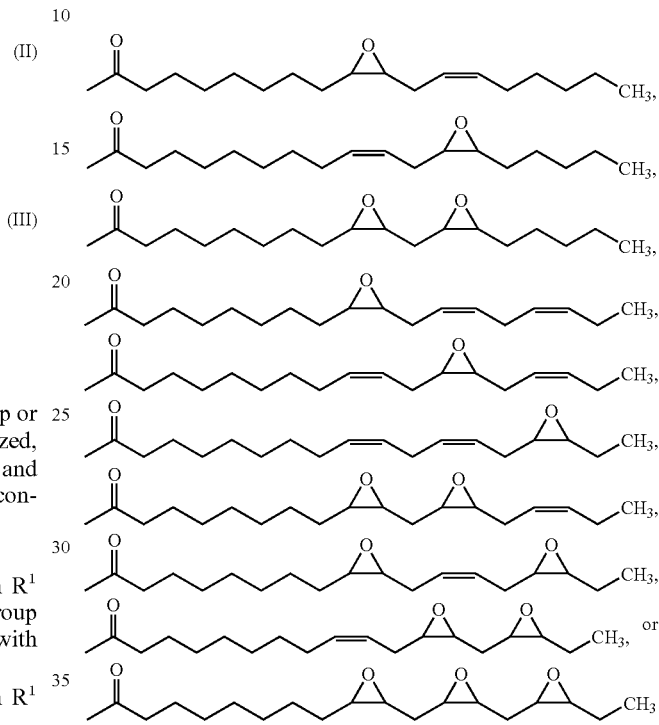

[wherein asymmetric carbon means R-configuration, S-configuration or a mixture thereof in any ratio.];

[32] A compound obtained by using the method depicted in above [1] and/or the kit depicted in above [13], a salt thereof or a solvate thereof;

[33] A composition for cell culture which comprises a compound represented by formula (I), (II) or (III):

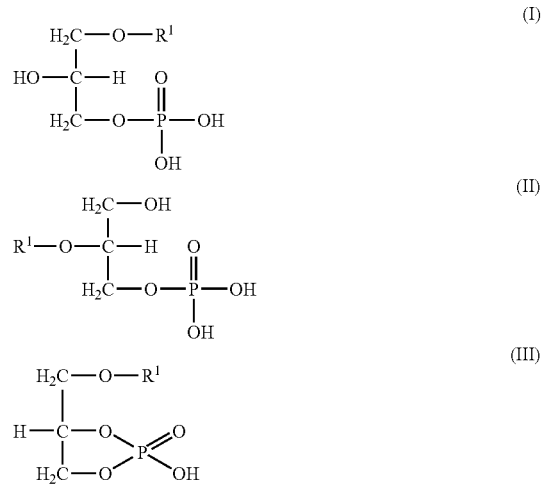

[wherein R¹ represents an aliphatic hydrocarbon group or an aliphatic hydrocarbon-carbonyl group which is oxidized, nitrated, nitrosated, nitrohydrylated and/or aminated, and wherein asymmetric carbon means R-configuration, S-configuration or a mixture thereof in any ratio.],
a salt thereof or a solvate thereof;

[34] The composition according to above [33], which is the agent for regulation of cell differentiation; and

[35] A chemically or enzymatically process for production of a compound represented by formula (I), (II) or (III):

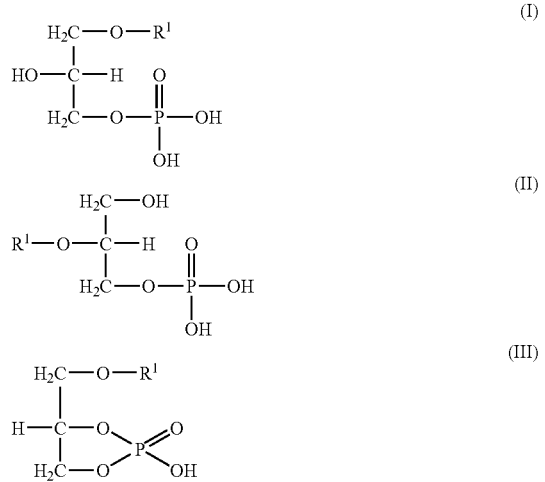

[wherein R¹ represents an aliphatic hydrocarbon group or an aliphatic hydrocarbon-carbonyl group which is oxidized, nitrated, nitrosated, nitrohydrylated and/or aminated, and wherein asymmetric carbon means R-configuration, S-configuration or a mixture thereof in any ratio.],
a salt thereof or a solvate thereof;
and the like.

In the present invention, LPA means the substance represented by above-mentioned formula (I), (II) or (III) of which R¹ represents the "unsubstituted aliphatic hydrocarbon group" or the "unsubstituted aliphatic hydrocarbon-carbonyl group" and it may be a natural substance or an artificial substance. Herein, the "unsubstituted aliphatic hydrocarbon group" means the straight chain group consisting of only carbon atom and hydrogen atom, and it may include, for example, alkyl, alkenyl, alkynyl group and the like. And the "unsubstituted aliphatic hydrocarbon group" may comprise the cycloaliphatic hydrocarbon-like group in it. The "cycloaliphatic hydrocarbon-like group" means the divalent group which is made by exclusion of two hydrogen atoms from the cycloaliphatic group (such as lower cycloalkane, lower cycloalkene and the like). The "lower cycloalkane" includes, for example, C3-8 cycloalkane and the like such as cyclopropane, cyclobutane, cyclopentane, and cyclohexane. The "lower cycloalkene" includes, for example, C3-8 cycloalkene and the like such as cyclopropene, 1-cyclopentene, 2-cyclopentene, 3-cyclopentene, 1-cyclohexene, 2-cyclohexene, 3-cyclohexene, and 3-cycloheptene. As the aliphatic hydrocarbon group which comprises the cycloaliphatic hydrocarbon-like group in it, for example, 7-(2-hexylcyclopropyl)heptyl group can be cited. The "alkyl group" includes, for example, C1-30 straight alkyl group such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl group and the like. The "alkenyl group" includes, for example, C2-30 straight alkenyl group such as ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, tricosenyl, teltacosenyl, pentacosenyl, hexacosenyl, heptacosenyl, octacosenyl, nonacosenyl, triacontenyl group and the like. The "alkynyl group" includes, for example, C2-30 straight alkynyl group such as ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl, nonacosynyl, triacontynyl group and the like.

In the present invention, the "unsubstituted aliphatic hydrocarbon-carbonyl group" means the monovalent group which is carbonyl group bound by the above-mentioned "unsubstituted aliphatic hydrocarbon group".

In the present invention, LPA may be expressed by using both the number of carbon atom(s) which consists the carbon chain of R¹ and the number of double bond(s) of R¹. For example, when the number of carbon atom(s) which consists the carbon chain of R¹ is 18 and the number of double bond(s) of R¹ is 1, that is, it may be named as 18:1-LPA.

In the present invention, as the preferable LPA, the naturally existing one can be cited.

And, in the present invention, as the preferable LPA, for example, 16:1-LPA, 18:1-LPA, 18:2-LPA, 18:3-LPA, 20:1-LPA, 20:2-LPA, 20:3-LPA, 20:4-LPA, 20:5-LPA, 22:1-LPA, 22:2-LPA, 22:3-LPA, 22:4-LPA, 22:5-LPA, 22:6-LPA and the like, which are represented by above-mentioned notational system, can be cited.

In the present invention, as more preferable LPA, LPA which exists in living body of mammal (especially human), for example, 22:6-LPA, 20:5-LPA, 20:4-LPA, 18:1-LPA, 18:2-LPA, 18:3-LPA, 16:1-LPA, and the like can be cited. More specifically, for example, the compound represented by formula (I), (II) or (II) of which R¹ represents cis-$\Delta^9$-octadecenoyl, cis,cis-$\Delta^9,\Delta^{12}$-octadecadienoyl, all cis-$\Delta^9$, $\Delta^{12}$, $\Delta^{15}$-octadecratrienoyl, all cis-$\Delta^5,\Delta^8$, $\Delta^{11},\Delta^{14}$-eicosatetraenoyl, n-dodecanoyl, n-tetradecanoyl, n-hexadecanoyl, n-octadecanoyl, trans-$\Delta^9$-octadecenoyl, cis-$\Delta^9$-hexadecenoyl, cis-$\Delta^6$-octadecenoyl, (9Z)-9-octadecen-1-yl, (9Z,12Z)-9,12-octadecadien-1-yl, (9Z, 12Z, 15Z)-9,12,15-ctadecatrien-1-yl, (5Z,8Z,11Z, 14Z)-5,8,11,14-eicosatetraen-1-yl, n-dedecyl, n-tetradecyl, n-hexadecyl, n-octadecyl, (9E)-9-octadecen-1-yl, (9Z)-9-hexadecen-1-yl, (6Z)-3-octadecen-1-yl, and the like can be cited.

In the present invention, the highly active LPA has to be a substance which binds to LPA receptor and shows substantially equal or more activity than LPA and of which structure is different from above-mentioned LPA, and the structure is not limited. Herein, the "substance which shows substantially equal or more activity than LPA" means, for example, the substance which shows about 1-fold to about 10-fold, preferably about 1-fold to about 100-fold, more preferably about 1-fold to about 1000-fold activity than known ligand of LPA receptor, LPA, in activity of (I) receptor binding or (2) signal transduction, etc. In the present invention, the highly active LPA needs not show activities more than LPA in all the activity-measuring systems, and only has to show activity more than LPA in at least one system that is able to detect the activity of LPA. The measurement of activity of receptor binding or signal transduction is able to conduct pursuant to known method. For example, it is able to conduct pursuant to the method of screening as described later or the method described in Examples.

In the present invention, the highly active LPA as more preferable includes, for example, the substance represented by above-mentioned formula (I), (II) or (III) of which $R^1$ represents an aliphatic hydrocarbon group or an aliphatic hydrocarbon-carbonyl group which is oxidized, nitrated, nitrosated, nitrohydrylated and/or aminated. Herein, as the aliphatic hydrocarbon group, for example, the one exemplified as the "unsubstituted aliphatic hydrocarbon group" can be cited. For example, the aliphatic hydrocarbon-carbonyl group has the same meanings as the above-mentioned "unsubstituted aliphatic hydrocarbon-carbonyl group". The term "oxidation" means the addition of at least One oxygen atom to the target molecule (herein, it means the aliphatic hydrocarbon group or the aliphatic hydrocarbon-carbonyl group), and is not limited by increase and decrease of other atom(s). Specifically, it means that the aliphatic hydrocarbon group or the aliphatic hydrocarbon-carbonyl group changes into the one having the oxygen atom-containing group such as hydroxy group (—OH), oxo group (=O), hydroperoxy group (-OOH), epoxy group (the oxygen atom which binds to two carbon atoms in the chain (—O—)), epidioxy group (the oxygen atom which binds to two carbon atoms in the chain (—O—O—)), formyl group (—CHO), and the like. And the carbon chain of the aliphatic hydrocarbon group or the aliphatic hydrocarbon-carbonyl group may be cut along with this "oxidation". The term "nitration" means the addition of nitro group (—NO$_2$) The term "nitrosation" means the addition of nitroso group (—NO). The term "nitrohydrylation" means the addition of both nitro group and hydroxy group to the same carbon atom. The term "amination" means the "addition of amino acid", and the term "addition of amino acid" means the addition of arbitrary amino acid. The amino acid to be added is not limited, and it may be peptide. Preferably, the amino acid existing in living body normally (for example, α-amino acid and the like) and the peptide thereof can be cited. The number of amino acid which composes the peptide is not limited. Preferably 2 to 10, more preferably 2 to 5, most preferably 2 (namely dipeptide) to 3 (namely tripeptide) and the like can be cited. The amino acid to be added preferably, for example, cysteine, serine, glutathione, glycylcysteine, 5-glutamylcysteine and the like can be cited. As in previously described "oxidation", the carbon chain of the aliphatic hydrocarbon group or the aliphatic hydrocarbon-carbonyl group may be cut along with these "nitration", "nitrosation", "nitrohydration" or "amination".

Thus, in the present invention, as the preferable highly active LPA, it can be cited that the one represented by above-mentioned formula (I), (II) or (III) of which $R^1$ represents the "unsubstituted aliphatic hydrocarbon group" or the "unsubstituted aliphatic hydrocarbon-carbonyl group" containing one or more part(s) selected from

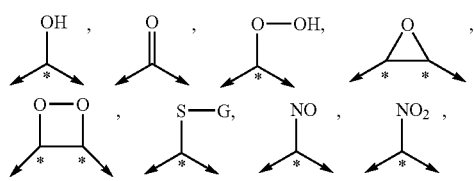

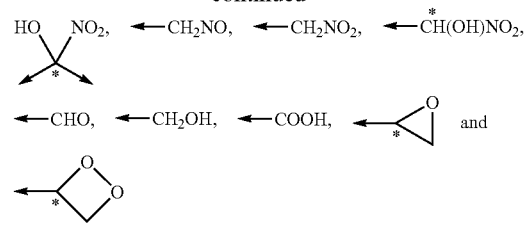

[wherein * represents an asymmetric carbon atom, and the carbon atom may be R-configuration, S-configuration or a mixture thereof in any ratio, and all other symbols have the same meanings as above.].

In addition, the asymmetric carbon atom is often represented by using the symbol "*" as previously described in the present invention, and in the case of not marking asymmetric carbon atom with "*", the symmetric carbon atom may mean R-configuration, S-configuration or a mixture thereof in any ratio if person skilled in the art can judge so.

In the present invention, as the more preferable highly active LPA, the one represented by above-mentioned formula (I), (II) or (III) of which $R^1$ represents:

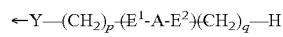

[wherein all symbols have the same meanings as above.] can be cited. Specifically, the one of which $R^1$ represents:

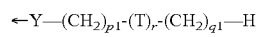

[wherein all symbols have the same meanings as above.] can be cited preferably, and the one of which at least one of T represents:

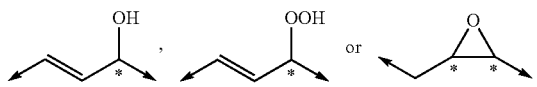

[wherein all symbols have the same meanings as above.] is most preferable.

Also, in the present invention, the one having been oxidized of LPA cited as preferable LPA too. For example, the oxidized-type of 22:6-LPA, 20;4-LPA, 18:1-LPA, 18:2-LPA, 18:3-LPA, 16:1-LPA and the like are preferable. For example, 20:4-LPA, 18:1-LPA, 18:2-LPA, 18:3-LPA and the like are more preferable.

Among these, especially in the case that the number of carbon atom of $R^1$ is 18, the one of which $R^1$ is an aliphatic hydrocarbon-carbonyl group represented by —C$_{18}$H$_{31}$O$_3$ or —C$_{18}$H$_{29}$O$_3$ is preferable. Specifically, the one of which $R^1$ is a C18 aliphatic hydrocarbon-carbonyl group which contains 2 to 3 double bonds and is substituted with 1 hydroperoxy group is preferable. Concretely, the compound represented by formula (I), (II) or (III) of which $R^1$ is:

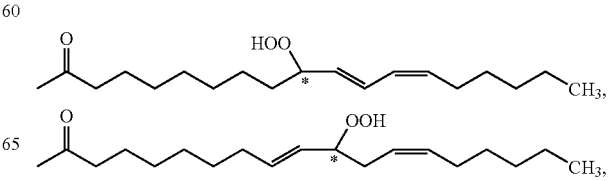

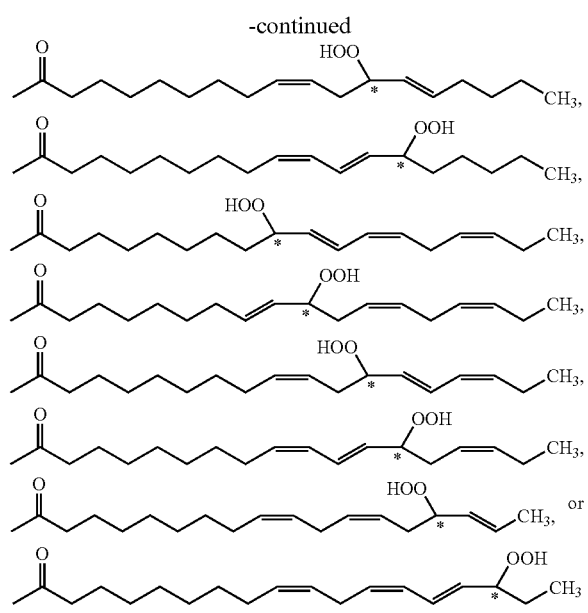

[wherein all symbols have the same meanings as above.] is preferable.

And also, the one of which $R^1$ is an aliphatic hydrocarbon-carbonyl group represented by —$C_{18}H_{31}O_2$, —$C_{18}H_{31}O_3$, —$C_{18}H_{29}O_2$, —$C_{18}H_{29}O_3$ or —$C_{18}H_{29}O_4$ is preferable. Specifically, the one of which $R^1$ is a C18 aliphatic hydrocarbon-carbonyl group which contains 0 or 1 to 2 double bond(s) and is substituted with 1 to 3 epoxy group(s) is preferable. Concretely, the compound represented by formula (I), (II) or (III) of which $R^1$ is:

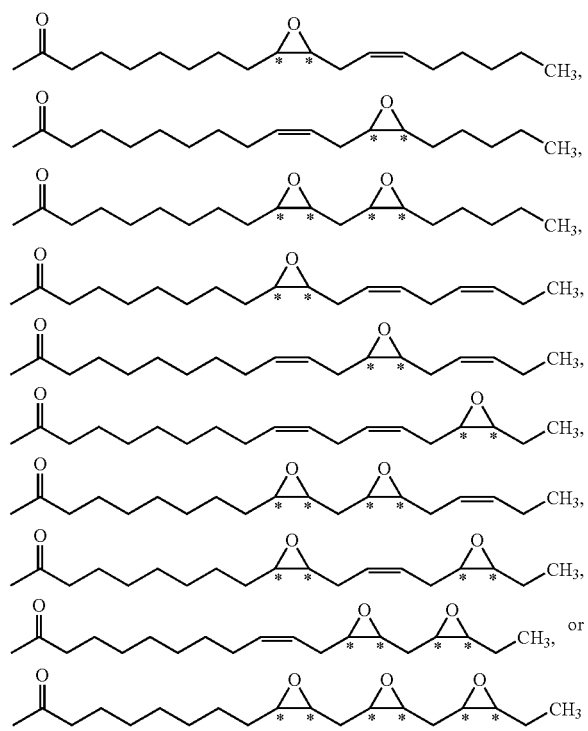

[wherein all symbols have the same meanings as above.] is preferable.

In the present invention, as C1-4 alkylene, for example, methylene, ethylene, trimethylene, tetramethylene and isomers thereof can be cited.

In the present invention, as C2-4 alkenyene, for example, ethenylene, propenylene, butenylene and isomers thereof can be cited.

In the present invention, the preferable highly active LPA may be defined by the length of carbon chain of $R^1$. Specifically, the one of which the number of carbon atom of main chain of $R^1$ is 6 to 26 and the like is preferable as the highly active LPA. Herein, the carbonyl carbon atom of the aliphatic hydrocarbon-carbonyl group is counted as the number of carbon atom of main chain. Thus, C6-26 alkyl, C6-26 alkenyl, C6-26 alkynyl, C6-25 alkylcarbonyl, C6-25 alkenylcarbonyl, C6-25 alkynylcarbonyl group and the like which is oxidized, nitrated, nitrosated, nitrohydrylated and/or aminated are preferable as $R^1$. Especially, oxidized these groups are preferable. For example, the one of which the carbon atom of main chain of $R^1$ is 10 to 20 and the like is more preferable, and for example, the one of which the carbon atom of main chain of $R^1$ is 6 to 20 and the like is especially preferable.

In the present invention, the above-mentioned highly active LPA can be obtained by the following method. For example, it can be obtained by any method of (1) chemical synthesis; (2) purification from biological sample; (3) enzymatically synthesis; and the like.

When the method of chemical synthesis is used, it can be obtained by the optimized and/or combined method of the known method such as the method described in Comprehensive Organic Transformations: A Guide to Functional Group Preparations, 2nd Edition (Richard C. Larock, John Wiley & Sons Inc., 1999) and the like, or by oxidation of the above-mentioned LPA. In order to oxidize LPA, it may be carried out by using oxidizing agent or by reaction with oxygen. In order to oxidize LPA by oxidizing agent, it may be carried out by addition of appropriate oxidizing agent (e.g., m-chloro perbenzoic acid) to any solvent (for example, water or an organic solvent (e.g., chloroform, methanol, acetonitrile, and the like)) which is containing LPA. In order to react with oxygen, it may be carried out by contact with oxygen gas, or by air oxidation. Also, it may be carried out by reaction with dissolved oxygen in any solvent. For example, it may be obtained by preservation of LPA adsorbed to appropriate container (for example, glass container that is able to provide surface area in a way such as kjeldahl-shaped flask) under unwatered air stream at the appropriate temperature (e.g., room temperature), or by incubation of any solvent (for example, water or an organic solvent (e.g., chloroform, methanol, acetonitrile, and the like)) which is containing LPA for any period (for example, from 24 hours to several days) at the appropriate temperature (preferably, room temperature and the like).

Purification from biological sample is able to be carried out by the known method, for example, purification of the fraction obtained by gel filtration, using silica gel column chromatography or using reverse phase column chromatography. Also, when the target highly active LPA is obtained as mixture, it can be isolated by the known purification method. For example, it can be isolated by the silica gel chromatography using silica gel (e.g. Merck7734 and the like) as a carrier, and using appropriate solvent (e.g., mixed solvent of chloroform, methanol and water). As biological sample, for example, blood can be used preferably.

When the method of enzymatically synthesis is used, for example, myeloperoxidase, oxidative enzyme, 12/15-lipoxigenase, P450 metabolic enzyme, and the like can be used.

LPA, as a raw material used in these process for production, can be obtained by enzymatically treatment of lysophosphatidylcholine with enzyme such as phospholipase D and the like as described in following Reference Example, or by above-mentioned known method for purification furthermore.

In the present invention, there is no particular limitation on the LPA receptor protein, as far as it is able to both bind to the above LPA and transmit intracellular signal to the cell expressing the LPA receptor protein. As the receptor protein like that, EDG-2, EDG-4, EDG-7, GPR23 and the like, known commonly as LPA receptor protein may be preferably used. The protein which has a substantially equivalent ability to that of these proteins or has a substantially same amino acid sequence as that of these proteins is also may be used. In addition, EDG-2, EDG4 and EDG-7 may be sometimes called LPA1, LPA2 and LPA3 respectively. Here, the "protein which has a substantially equivalent ability" includes, for example, the protein which has the ligand binding activity, the signal transduction activity of the same nature. Therefore, as the "protein which has a substantially equivalent ability", the protein which has the ligand binding activity and the signal transduction activity and the like are equivalent (such as about 0.01 times to about 100 times, preferably about 0.5 times to about 20 times, more preferably about 0.5 times to about 2 times) to that of the above-mentioned known receptor protein, namely EDG-2, EDG-4, EDG-7, GPR23 and the like is preferable, but the degree of the activity and the quantitative factor such as protein molecular weight and the like may be different. The measurement of the ligand binding activity and the signal transduction activity and the like may be carried out according to a method based on the known ones. For example, it may be carried out by the screening method described below. The "substantially same amino acid sequence" includes, for example, the protein which shares more than about 50%, preferably more than about 60%, more preferably more than 70%, moreover preferably more than about 80%, much more preferably more than about 90%, most preferably about 95% amino acid homology with the above known receptor protein i.e. EDG-2, EDG-4, EDG-7, GPR23 and the like.

In the present invention, there is no particular limitation on the derivation of the above-mentioned LPA receptor protein. For example, the derivation of the protein may include every cell (such as splenocyte, neurocyte, neuroglial cell, pancreatic β cell, bone marrow cell, mesangial cell, Langerhans cell, epidermal cell, epithelial cell, endothelial cell, fibroblast, fiber cell, muscular cell, adipose cell, immunocyte [such as macrophage, T cell, B cell, natural killer cell, mast cell, neutrophil, basophil, eosinophil, monocyte], megakaryocyte, synoviocyte, chondrocyte, osteocyte, osteoblast, osteoclast, breast cell, hepatocyte, or stromal cell, or precursor cell thereof, or stem cell thereof, or cancer cell thereof), hemocyte family, or every tissue including one or some of the above cells (such as brain, each region of brain [such as bulbus olfactorius, amygdaloid nucleus, basal ganglion, hippocampus, thalamus, hypothalamus, subthalamic nucleus, cerebral cortex, medulla oblongata, cerebellum, occipital lobe, frontal lobe, temporal lobe, putamen, caudate nucleus, callosum, substantia nigra], spinal cord, pituitary gland, stomach, pancreas, kidney, liver, gonad, thyroid, cholecyst, bone marrow, adrenal gland, skin, muscle, lung, gastrointestinal tract [such as colon, small intestine], blood vessel, heart, thymus, spleen, submandibular gland, peripheral blood, peripheral hemocyte, prostate gland, testicle, orchis, ovary, placenta, uterus, bone, joint, skeletal muscle) of human or mammal (such as guinea pig, rat, mouse, rabbit, pig, sheep, cattle, monkey, and the like). In addition, the protein may be made by artificial protein synthesis.

Moreover, the LPA receptor protein of the present invention may include, for example, a receptor protein containing the modified amino acid sequence of the above LPA receptor protein, by such as addition, deletion and/or substitution of several amino acids, besides the above-mentioned LPA receptor protein. If necessary, it also may have a functional group substituted with an arbitrary substituent (such as carboxyl group, amino group, hydroxyl group, thiol group) or bind sugar chain within the molecule, to the extent that it loses the function as a receptor.

In the present invention, there is no particular limitation on the partial petide of the above-mentioned receptor protein (hereinafter referred to as "partial peptide"), as far as it is the partial peptide of the above-mentioned receptor protein or it has a substantially same amino acid sequence as that of the partial peptide. Among the above-mentioned receptor protein element, the partial peptide which both constitutes a part of extracellular site and has a substantially equivalent activity of ligand binding may be used preferably. The partial peptide of the above-mentioned receptor protein, i.e. the partial protein of EDG-2, EDG-4, EDG-7, GPR23 and the like, includes for example, the peptide containing the site which is determined as an extracellar region (hydrophilic region) by hydrophobic moment plot methodology. In addition, it also includes, the peptide containing a part of hydrophobic site, each domain individually, and plural domains together. The number of the amino acid encoding the partial peptide used in the present invention is at least more than 20, preferably more than 50, more preferably more than 100 of the amino acid sequence encoding the above receptor protein. Here, the "substantially same amino acid sequence" means the amino acid sequence which shares more than about 50%, preferably more than about 60%, more preferably more than about 70%, moreover preferably more than about 80%, much more than preferably about 90%, most preferably more than about 95% homology with the partial peptide of the above-mentioned receptor protein. In addition, the "substantially equivalent activity of ligand binding" means the ligand binding activity of the same nature, and it may be measured by the same method of measuring the ligand binding activity of the above-mentioned receptor protein.

Furthermore, the partial peptide of the present invention includes, besides the above-mentioned partial peptide, for example, a partial peptide containing modified amino acid sequence of the above-mentioned partial peptide by, such as addition, deletion and/or substitution of several amino acids. If necessary, it also may have a functional group substituted with an arbitrary substituent (such as carboxyl group, amino group, hydroxyl group, thiol group) or bind sugar chain within the molecule, to the extent that it does not lose the ligand binding activity.

In the present invention, as the salt of the above-mentioned receptor protein or the partial peptide thereof, the physiologically acceptable salt with acid or base and the like can be cited. Especially, the physiologically acceptable acid-addition salt is preferable. As the salt like this, for example, salt with inorganic acid (for example, hydrochloric acid, phosphoric acid, hydrobromic acid, sulfuric acid, and the like) or organic acid (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid, and the like) are used.

In the present invention, the above-mentioned LPA receptor protein, the partial peptide thereof, or the salt thereof can be obtained by the known method. The LPA receptor protein or the salt thereof can be produced by the known purification method of receptor protein from cell or tissue of human or mammal as described above. Also, it can be produced by culture of transformant comprising DNA which codes the receptor protein. Moreover, it also can be produced by the known method for protein synthesis or the according method. The method of obtaining LPA receptor protein is disclosed circumstantially in WO 97/00952, WO 96/39436, Toku-KaiHei 10-210993, TokuKaiHei 11-18788, WO 99/29887, WO 99/24569, and the like. In case of producing from tissue or cell of human or mammal, it can be purified and isolated by homogenization of tissue or cell of human or mammal, subsequent extraction with acid etc., and chromatography of obtained extract using reversed phase chromatography, ion-exchange chromatography or combination of them. The partial peptide or the salt thereof of the present invention can be produced by the known method for peptide synthesis, or by digestion of the protein of the present invention by appropriate peptidase. As the method for peptide synthesis, for example, solid phase peptide synthesis, liquid phase peptide synthesis, and the like can be used.

In the present invention, as the substance for labelling of the highly active LPA, for example, radioisotope, enzyme, fluorescent material, light-emitting material, and the like can be used. As the radioisotope, for example, $^{125}I$, $^{131}I$, $^{3}H$, $^{14}C$, $^{32}P$, and the like can be used. As the enzyme, for example, β-galactosidase, β-glucosidase, alkaline phosphatase, peroxidase, malate dehydrogenase, and the like can be used. As the fluorescent material, for example, fluorescamine, fluorescein isothiocyanate, and the like can be used. As the light-emitting material, for example, luminol, luminol derivative, luciferin, lucigenin, and the like can be used.

The highly active LPA of the present invention is safe and less toxic, so it can be used as tool for screening.

The method of screening of the present invention is characterized by using both (1) the optionally labelled highly active LPA and (2) the LPA receptor protein, the partial peptide thereof, or the salt thereof. The present invention includes all cases where the substance having the special function, for example, the preventive and/or therapeutic substance for diseases in which LPA takes part, is discovered by using these substance. The screening method of the present invention is conducted by comparing (1) the instance after contacting (a) the labelled highly active LPA and (b) the LPA receptor protein, the partial peptide thereof, or the salt thereof, to (2) the one after contacting (a) the labelled highly active LPA, (b) the LPA receptor protein, the partial peptide thereof, or the salt thereof and (c) the testing compound. Herein, the LPA receptor protein, the partial peptide thereof, or the salt thereof used in the method of screening of the present invention may be in whatever status, if it does not lose the activity for ligand binding. For example, what is isolated or is expressed in the cell may be included. Also, membrane fraction that is prepared from the cell or whole body (e.g., mammal etc.) may be included. In the method of screening of the present invention, the method for measuring the binding between the LPA receptor protein, the partial peptide thereof, or the salt thereof and the highly active LPA as ligand may be changed depending on the status of the LPA receptor protein, the partial peptide thereof, or the salt thereof. If it is isolated, or is membrane fraction, or is expressed on the cell, binding assay can be used. Also, if it is expressed on the cell, the phenomenon that comes about in the cell (for example, increase and decrease of intracellular concentration of cyclic AMP (cAMP) or calcium ion, increase and decrease of specific protein or mRNA that codes it, or extracellular secretion of specific protein, and the like) is used as indicator. If using mammal (for example, mouse, rat, dog, and the like), the phenomenon that comes about in the living body is used as indicator. Also, if desired, it can be evaluated by using specific tissue removed firm the living body. For example, it may be the magnus test using trachea or other smooth muscle or intestinal tract or the like.

In the present invention, the method described in following [I]-[IV] can be cited as the preferable method of screening. [I] The method of screening which comprises comparing (1) the measured increase of intracellular concentration of calcium ion of the cell after contacting (a) the optionally labelled highly active LPA and (b) the cell which comprises the LPA receptor protein, to (2) the one after contacting (a) the optionally labelled highly active LPA, (b) the cell which comprises the LPA receptor protein and (c) the testing compound. [II] The method of screening, which comprises comparing (1) the amount of the labelled highly active LPA which is bound to the LPA receptor protein, the partial peptide thereof, or the salt thereof after contacting (a) the labelled highly active LPA and (b) the LPA receptor protein, the partial peptide thereof, or the salt thereof, to (2) the one after contacting (a) the labelled highly active LPA, (b) the LPA receptor protein, the partial peptide thereof, or the salt thereof and (c) the testing compound. [III] The method of screening, which comprises comparing (1) the amount of the labelled highly active LPA which is bound to the cell after contacting (a) the labelled highly active LPA and (b) the cell which comprises the LPA receptor protein, to (2) the one after contacting (a) the labelled highly active LPA, (b) the cell which comprises the LPA receptor protein and (c)the testing compound. [IV] The method of screening, which comprises comparing (1) the amount of the labelled highly active LPA which is bound to the membrane fraction of the cell after contacting (a) the labelled highly active LPA and (b) the membrane fraction of the cell which comprises the LPA receptor, to (2) the one after contacting (a) the labelled highly active LPA, (b) the membrane fraction of the cell which comprises the LPA receptor and (c) the testing compound. The measurement of the bonding amount, in other words, the binding assay or the measurement of activity of increase in intracellular calcium concentration is able to be measured by using the known method or using the commercially available kit for measurement In the above-mentioned method of screening, if the cell that comprises the LPA receptor protein is used, and the measurement of activity of increase in intracellular calcium concentration is used as indicator, the method that comprises (1) culture of the cell which comprises the LPA receptor protein on multiwell-plate and the like, (2) optionally change of medium to flesh medium or appropriate buffer which is non-toxic for the cell, (3) incubation for definite period of time after addition of the highly active LPA of the present invention, and (4) measurement of calcium concentration of extract of the cell, is used preferably.

In the above-mentioned method of screening, if the cell that comprises the LPA receptor protein or the membrane fraction thereof is used, the cell may be used after fixation by glutaraldehyde or formalin and the like. The fixation is conducted in accordance with the known method. As the cell that comprises the LPA receptor protein, a host cell that comprises the LPA receptor protein is used preferably. Herein, as the host cell, *Escherichia coli, Bacillus subtilis*, yeast, insect cell, animal cell, or the like is used preferably. Also, it is possible to use normal cell, if the expression level of the LPA receptor protein is enough to apply to a screening system, The membrane fraction means the fraction which comprises much of cell membrane obtained by the known method after cell lysis. As the method for cell lysis, the method that crushes the cell by Potter-Elvehjem homogenizer, the method that crushes by waring blender or POLYTRON (manufactured by Kinematica), the method that crushes by ultrasonic, the method that crushes by spout of the cell from narrow nozzle under pressurization by French press, or the like can be cited. The method for fractionation of the cell membrane, fractional method using centrifugal force such as differential centrifugation or density-gradient centrifugation, or the like can be used preferably. For example, the cell lysate is centrifuged at low speed (e.g., about 500 rpm to about 3000 rpm) for a short time (e.g., about 1 minutes to about 10 minutes), and the supernatant is centrifuged at higher speed (e.g., about 15000 rpm to about 30000 rpm) for about 30 minutes to about 2 hours usually, and obtained residue is used as membrane fraction. The LPA receptor protein which is expressed and the membrane component such as phospholipid derived from the cell or the membrane protein or the like are much included in the membrane fraction. It is preferable that the amount of the LPA receptor protein in the cell which comprises the LPA receptor protein or in the membrane fraction is $10^3$ to $10^8$ molecules (more preferable one is $10^5$ to $10^7$ molecules) per 1 cell. In addition, the more expression level is high, the more ligand (that is, LPA or the highly active LPA) binding activity per membrane fraction (specific activity) is high, so it is able to not only establish a sensitive screening system but also measure a large amount of sample by using same lot.

In the compound which has a binding activity to the LPA receptor obtained by using the method of screening of the present invention, an agonist and an antagonist to the LPA receptor are included. To select the agonist or the antagonist to the LPA receptor from the group of compounds which have the binding activity to the LPA receptor, for example, it only has to test such as (1) to confirm the possibility of signal transduction in the presence of the compound only; (2) to confirm the possibility of signal transduction in the presence of the compound, in case where LPA or the highly active LPA is added; and the like. To ascertain presence of action of signal transduction, it can be confirmed by using the phenomenon which comes about in the cell, in the tissue, or in the living body as an indicator as previously described.

In the present invention, the screening kit for a preventive and/or therapeutic substance for diseases in which LPA takes part, which comprises using an optionally labelled highly active LPA is mainly made up of both (a) the optionally labelled highly active LPA, and (b) the cell or membrane fraction thereof which comprises the LPA receptor protein. As examples of the screening kit of the present invention, for example, the following one is cited.

1. Reagent for Screening
(a) Measuring Buffer and Washing Buffer: That made by addition of bovine serum albumin (manufactured by Sigma) at the concentration of 0.05% to Hank's Balanced Salt Solution (manufactured by Gibco). That is sterilized by filtration with filter of pore size 0.45 μm and stored at 4° C., or may be prepared as necessary.
(b) The standard of the LPA receptor protein: That made by culture of Chinese Hamster Ovary (CHO) cell which is expressed the LPA receptor protein on 12-well plate at the cell density of $5\times10^5$ cells/well for 2 days at 37° C., 5% $CO_2$, 95% air.
(c) The labelled highly active LPA: That is the solution comprising the highly active LPA labelled by commercially available [$^3$H], [$^{125}$I], [$^{14}$C], [$^{35}$S], or the like. That is stored at 4° C. or –20° C., and if necessary, diluted with measuring buffer to the concentration of 1 μM.
(d) The standard of the highly active LPA: That is made by dissolving the highly active LPA to PBS comprising 0.1% bovine serum albumin (manufactured by Sigma) at the concentration of 1 mM and stored at –20° C.

2. Method for Measuring
(a) Chinese Hamster Ovary (CHO) cells which expresses the LPA receptor protein cultured on 12-well tissue culture plate are washed two times by measuring buffer (1 mL) and 490 μL of measuring buffer is added to the each well.
(b) After addition of 5 μL of test compound solution ($10^{-3}$ M to $10^{-10}$ M), 5 μL of the labelled highly active LPA is added and incubate for 1 hour at room temperature. In order to estimate the amount of non-specific binding, 5 μL of the highly active LPA ($10^{-3}$ M) is added instead of test compound.
(c) The reaction solution is removed and wash three times by 1 mL of washing buffer. The labelled highly active LPA bound to the cell is lysed by 0.2 N NaOH –1% SDS, and mixed with 4 mL of liquid scintillator A (manufactured by Wako).
(d) The radioactivity is measured by using liquid scintillation counter (manufactured by Beckman) and Percent Maximum Binding (PMB) is calculated by the formula {PMB= [(B–NSB)/(B0–NSB)]×100}. Herein, PMB means Percent Maximum Binding, B means the value obtained in the presence of test substance, NSB means Non-specific Binding, and B0 means the amount of maximum binding.

In the present invention, there is no particular limitation on the antibody against highly active LPA, as far as it can recognize the highly active LPA. There is no preference whether the antibody is polyclonal or monoclonal. The antibody against highly active LPA of the present invention may be prepared according to the known method of preparing an antibody or an antiserum, using (1) the highly active LPA of the present invention, (2) complex of the highly active LPA with carrier protein, (3) complex of a derivative which has an amino group or a carboxyl group on the side chain of the highly active LPA with carrier protein, or the like as an antigen. One of the concrete method is shown below.

Preparation of the Monoclonal Antibody:

(a) Preparation of the Monoclonal Antibody-producing Cell

The highly active LPA of the present invention may be administered to mammalian either alone or with carrier or dilution agent. On the purpose of enhancing the capacity to produce antibodies, complete Freund's adjuvant or incomplete Freund's adjuvant may be administered at the time of administration. The frequency of administration is generally once every 2 to 6 weeks and the total is 2 to 10 times. The mammal species which may be used includes, for example, monkey, rabbit, dog, guinea pig, mouse, rat, sheep, and goat and preferably is mouse and rat. Furthermore, there is no particular limitation on an administration site, as far as it is the site where the antibody may be produced. The preparation of the monoclonal antibody producing-cell may be carried out by selecting individuals that show a positive antibody titer from the antigen-immunized warm-blooded animals, such as mice, taking the spleen or the lymph node 2 to 5 days after the final immunization and fusing the antibody producing-cells obtained from these tissues with myeloma cells in sequence to produce the monoclonal antibody producing-hybridoma cell. The measurement of the antibody titer in antiserum may be carried out by reacting to the above-mentioned labeled highly active LPA with antiserum and then measuring the activity of the labeled LPA bound to the antibody. The way to fuse with myeloma cells may be carried out according to a known method, such as the method of Köhler and Milstein (*Nature*, vol. 256, p 495, 1975). For example, polyethyleneglycol (PEG), Sendai virus and the like, preferably PEG and the like may be used for promoting the fusion. The above-mentioned myeloma cell includes, for example, NS-1, P3U1, and SP2/0. P3U1 is preferable. The preferable portion of the number of antibody producing-cell to the number of the myeloma cell is about 1:1 to 20:1. The cellular fusion may be effectively carried out by adding about 10 to 80% concentration of PEG (preferably PEG 1000 to PEG 6000) and incubating at about 20 to 40° C., preferably about 30 to 37° C. for about 1 to 10 minutes.

The screening of monoclonal antibody-producing-cells may be carried out by various methods. For example, the screening may be carried out by adding the culture supernatant of the hybridoma to the solid phase (such as microplate) absorbing the antigen like the highly active LPA, directly or with carrier, and then adding to anti-immunoglobulin antibody (in case where mouse-derived cell is used at the cellular fusion, anti-mouse immunoglobulin antibody is selected) or protein A which are labeled by radioactive substance, enzyme or the like in sequence to detect the monoclonal antibodies bound to the solid phase. As another method, it may be also carried out by adding the culture supernatant of the hybridoma to the solid phase absorbing anti-immunoglobulin antibody or protein A and then adding receptor protein labeled by a radioactive substance, enzyme or the like in sequence to detecting the monoclonal antibody bound to the solid phase. The selection of monoclonal antibody may be carried out by a known method or a method based on the known ones. Generally, it may be carried out in the medium for animal cell and the like containing HAT (hypoxanthine, aminopterin, thymidine). There is no particular limitation on the medium for the selection or breeding, as far as hybridoma can be grown. The medium includes, for example, RPMI-1640 medium containing 1 to 20%, preferably 10 to 20% of fetal bovine serum, GIT medium (manufactured by WAKO) containing 1 to 10% of fetal bovine serum and serum-free medium for hybridoma culture (SFM-101, manufactured by Nissui Co Ltd). The culture temperature is generally 20 to 40° C., preferably about 37° C. The culture period is generally 5 days to 3 weeks, preferably 1 week to 2 weeks. The culture may be carried out under the atmosphere of 5% $CO_2$ in general. The measurement of the antibody titer in hybridoma culture supernatant may be carried out by the same way of the above-mentioned method of measuring the antibody titer in antiserum.

(b) Purification of the Monoclonal Antibody

The separation and purification of monoclonal antibody may be generally carried out according to the way of the separation and purification of immunoglobulin, as in the separation and purification of polyclonal antibody. These purification method include, for example, salting-out method, alcohol precipitation method, isoelectric precipitation method, electrophoresis method, adsorption and desorption method using ion exchanger (such as DEAE), ultracentrifugal method, method of gel filtration chromatography, or specific purification method to obtain antibody by dissociating the binding after collecting antibody only by activated absorption agent such as antigen binding solid phase, Protein A or Protein G.

Preparation of the Polyclonal Antibody:

The polyclonal antibody may be produced by a known method or a method based on a known method. For example, it may be produced by forming the complex the highly active LPA as antigen with carrier protein, immunizing mammal in the same way of the above-mentioned method of producing monoclonal antibody, obtaining tissue which contains antibody against highly active LPA of the present invention from the immunized animal and then subjecting the antibody to separation and purification in sequence. As for the complex between antigen for immunizing mammal and carrier protein, there is no particular limitation on the kind of carrier protein and the mixing ratio of carrier to hapten, as far as the antibody can be effectively produced against the immunized hapten cross-linked carrier. Carrier includes, for example, bovine serum albumin, bovine thyroglobulin, keyhole limpet hemocyanin. The weight ratio of hapten to carrier is about 0.1 to 20, preferably about 1 to 5 for coupling. Various kinds of condensing agent may be used for the coupling of hapten to carrier. For example, glutaraldehyde, carbodiimide, maleimide active ester, and active ester agents containing thiol group, dithiopyridyl group are preferably used as the condensing agent. The condensation product is administrated to mammal either alone or with carrier or dilution agent. There is no particular limitation on an administration site, as far as it is the site where the antibody may be produced. On the purpose of enhancing the capacity to produce antibodies, complete Freund's adjuvant or incomplete Freund's adjuvant may be administered at the time of administration. The frequency of administration is generally once every 2 to 6 weeks and the total is about 2 to 10 times. The polyclonal antibody can be obtained from blood, ascites fluid and the like, preferably blood of the above-mentioned immunized mammal. The polyclonal antibody titer of antiserum can be measured in a similar way of the above-mentioned method for measuring of the antibody titer in antiserum. The separation and purification of polyclonal antibody may be carried out according to the method for the separation and purification of immunoglobulin which is same as that of monoclonal antibody described above.

In the present invention, the antibody against highly active LPA can be used for quantitative determination of the highly active LPA of test solution, especially quantitative determination by a sandwich immunoassay, because it can recognize the LPA specifically. The antibody against highly active LPA of the present invention may be used for diagnosis of diseases and the like. For example, it can be used for determination whether the disease is the disease in which LPA takes part by measuring the quantity of the highly active LPA in biological sample (preferably tissue of affected region, blood and the like) obtained from a patient in some disease, and then comparing the quantity to that of normal tissue or sample of normal person. In the case where the disease is the disease in which LPA takes part, it may be effectively treated by administering the neutralizing antibody shown below or the therapeutic substance for disease in which LPA takes part obtained by using the method or the screening kit of the present invention. Furthermore, as for biological sample obtained from normal person, if the quantity of the highly active LPA is more than that of normal person which is usually observed, the onset of the disease in which LPA takes part may be effectively prevented by administering the preventive substance for disease in which LPA takes part obtained by using the method or the screening kit of the present invention.

In the present invention, the neutralizing antibody against highly active LPA means the antibody which has the activities of both inhibiting the binding of the highly active LPA to the LPA receptor protein and inactivating the signal transduction through the LPA receptor protein. Therefore, in the case where the antibody against highly active LPA of the present invention is a neutralizing antibody, it can be used for inactivating signal transduction in which the highly active LPA and/or the LPA receptor takes part, such as LPA receptor protein-mediated cell stimulation activity (for example, accelerating or suppressing activity of release of arachidonic acid, release of acetylcholine, increase of intracellular calcium ion concentration, production of intracellular cyclic AMP (cAMP), production of intracellular cyclic GMP (cGMP), production of inositol phosphate, change in cell membrane potential, phosphorylation of intracellular protein, activation of c-fos, decrease of pH, and the like), other than the above purpose.

In the present invention, the highly active LPA can be used as the composition for cell culture by mixing with commonly used basal medium for cell culture, besides the above-mentioned screening method, the above-mentioned antibody production or the like. The composition for cell culture containing the highly active LPA functions as the controlling agent of cell differentiation, so it is able to make anaplastic cell differentiate into cell which has a certain function (differentiation-inducing activity), or make anaplastic cell not differentiate phenomenally autonomously or heteronomously (differentiation-inhibiting activity). Herein, the above anaplastic cell means the cell which expresses the above-mentioned LPA receptor protein and has an ability to grow by certain stimulation and has an ability to differentiate into the cell having certain function by certain stimulation. There is no particular limitation on its derivation. The derivation of the cell is generally animal, preferably mammal, more preferably human. For example, embryo-stem cell, ectodermal stem cell, mesodermal stem cell, endodermal stem cell, mesenchymal stem cell, hematopoietic stem cell, neural stem cell, neural precursor cell, hepatic stem cell, muscular stem cell, pancreatic stem cell, cutaneous stem cell, retinal stem cell, hair-follicular stem cell, osteo-progenitor cell, preadipocyte, chondrocyte, germinative cell, epidermal cell, vascular endothelial cell, smooth muscle cell, and the like and the cell which is genealogically same as these cell are preferably used.

There is no particular limitation on the basal medium for cell culture which may be mixed with the highly active LPA. For example, Dulbecco's modified Eagle medium, William's F, medium, Ham's F-10 medium, Ham's F-12 medium, RPMI-1640 medium, MCDB153 medium, 199 medium and the like, known as a basal medium traditionally, may be used. Furthermore, if necessary, antibiotic agent and antifungal agent may be added to basal medium for cell culture. If necessary, additives having differentiating activity in its own, for example, serum (such as fetal bovine serum (FBS), horse serum), insulin, EGF, FGF2, bFGF, interleukin (IL), stem cell factor (SCF), erythropoietin (EPO), interferon (IFN), thrombopoietin (TPO), tumor necrosis factor (TNF), colony stimulating factor (CSF), dexamethasone, β-glycerol phosphate, ascorbic acid, TGF-β, 1-methyl-3-isobutylxanthine, indomethacin, and the like can be added properly.

In the case of conducting cell culture using the composition for cell culture containing the highly activate LPA, the concentration of the highly active LPA, the treating duration, cell density, other culture condition (such as with or without coating of culture dish) and the like may be changed properly according to the kind of culturing cell. The way to examine whether the cells have been differentiated by culture using the composition for cell culture containing the highly active LPA or not, may be carried out by the known method. For example, a preferable method is the detection of a characteristic protein or mRNA and the like expressed in each differentiation stage.

The cell cultured with a composition for cell culture containing the highly active LPA may be used for various purposes. For example, it is able to produce the cell for transplantation by culture of anaplastic cell, which is obtained from living body, to differentiate using a composition for cell culture containing the highly active LPA.

Isomer:

Unless otherwise specified, the present invention includes all isomers. For example, alkyl, alkoxy, alkylene, etc. include straight or branched ones. In addition, the present invention also includes isomers on double bond, ring, fused ring (E-, Z-, cis-, trans-isomer), isomers generated from asymmetric carbon atoms (R-, S-isomer, α-, β-configuration, enantiomer, diastereomer), optically active isomers (D-, L-, d-, 1-isomer), polar compounds generated by chromatographic separation (more polar compound, less polar compound), equilibrium compounds, mixtures thereof at any ratios and racemic mixtures. Also, the present invention includes all isomers by tautomeric shift.

As previously described, the carbon atom of asymmetric center is represented by using the symbol "*" in the present invention. The carbon atom of which is marked with "*" may mean R-configuration, S-configuration or a mixture thereof in any ratio. And in the case of not marking asymmetric carbon atom with "*", the asymmetric carbon atom may mean R-configuration, S-configuration or a mixture thereof in any ratio if person skilled in the art can judge so.

In the present invention, the site of binding may be represented by arrowhead. In the structure which having two or more arrowheads, the arrowheads only have to bind to the site of binding, and the direction of binding are not limited, In the present invention, unless otherwise specified and as is apparent for those skilled in the art, the symbol ⋯ᐟ indicates that it is bound to the opposite side of the sheet (namely α-configuration), the symbol ⟋ indicates that it is bound to the front side of the sheet (namely β-configuration), the symbol ⟋ indicates that it is α-configuration, β-configuration, or a mixture thereof, and the symbol ⟋ indicates that it is a mixture of α-configuration and β-configuration.

Salts & Solvates

The compound obtained by using the method of screening or the screening kit of the present invention (hereinafter, referred to as "the compound derived from the present invention") may form the salt, the N-oxide, or the quaternary ammonium salts. Moreover, these compounds may be the solvates. Salts of the compound derived from the present invention include all non-toxic salts and pharmacologically acceptable salts. The pharmacologically acceptable salts are preferably non-toxic and water-soluble salts. Suitable salts include, for example, salts of alkali metals (potassium, sodium, lithium, etc.), salts of alkaline earth metals (calcium, magnesium, etc.), ammonium salts (tetramethylammonium salts, tetrabutylammonium salts, etc.), salts with organic amines (triethylamine, methylamine, dimethylamine, cyclopentylamine, benzylamine, phenethylamine, piperidine, monoethanolamine, diethanolamine, tris(hydroxymethyl)methylamine, lysine, arginine or N-methyl-D-glucamine, etc.) and acid addition salts [salts of inorganic acids (hydrochloride, hydrobromide, hydroiodide, sulfate, phosphate, nitrate, etc.), salts of organic acids (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.), and the like]. The N-oxides of the compound derived from the present invention mean compounds where nitrogen atom of the compound derived from the present invention is oxidized. And the N-oxides of the compound derived from the present invention may form the above-mentioned salts. The quaternary ammonium salts of the compound derived from the present invention mean compounds where a nitrogen atom of the compound derived from the present invention is quaternized by $R^0$ ($R^0$ represents an optionally substituted aliphatichydrocarbon group or an optionally substituted ring). The quaternary ammonium salts of the compound derived from the present invention may form the above-mentioned salts or the above-mentioned N-oxides. The appropriate solvates of the compound derived from the present invention, the salts thereof, the N-oxides thereof, or the quaternary ammonium salts thereof include, for example, solvates of water, alcohol solvents (ethanol, etc.), and the like. The solvates are preferably non-toxic and water-soluble one. The compound derived from the present invention can be converted to the above-mentioned salts, the above-mentioned N-oxides, the above-mentioned quaternary ammonium salts, or the above-mentioned solvates by any known method.

The highly active LPA of the present invention may form the salt or the solvate. As these salts and solvates, same salts or same solvates of the compound obtained by using the method of screening or the screening kit of the present invention can be used preferably.

Prodrugs:

In the present invention, the prodrug of the compound derived from the present invention means a compound which is converted to the compound derived from the present invention by reaction with an enzyme, a gastric acid, or the like, in the living body. Examples of the prodrug of the compound derived from the present invention include a compound wherein amino of the compound derived from the present invention is substituted with acyl, alkyl, phosphoric acid, or the like (e.g., a compound wherein amino of the compound derived from the present invention is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethy, tert-butyl, etc.); a compound wherein hydroxy of the compound derived from the present invention is substituted with acyl, alkyl, phosphoryl, boryl, or the like (e.g., a compound wherein hydroxy of the compound derived from the present invention is substituted with acetyl, palmitoyl, propanoyl, pivaloyl, succinyl, fumaryl, alanyl, dimethylaminomethylcarbonyl, etc.); a compound wherein carboxy of the compound derived from the present invention is esterified or amidated (e.g., a compound wherein carboxy of the compound derived from the present invention is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl) methyl ester, cyclohexyloxycarbonylethyl ester, methyl amide, etc.), and the like. These compounds may be prepared by per se known method. In addition, the prodrug of the compound derived from the present invention may be hydrate or non-hydrate. In addition, the prodrug of the compound derived from the present invention may be a compound which is converted into the compound derived from the present invention under the physiological conditions as described in Development of Medicine, Vol. 7 "Molecular Design", pages 163-198 published in 1990 by Hirokawa Publishing Co. In addition, the compound derived from the present invention may be labeled with an isotope (e.g., $^3H$, $^{14}C$, $^{35}S$, $^{125}I$, etc.) and the like.

Application to Medicaments:

The compound, the salt thereof, the solvate thereof or the prodrug thereof obtained by using the method of screening of the present invention or the screening kit of the present invention modulates the binding between the highly active LPA and the LPA receptor in mammals (for example, human or non-human animals such as monkey, sheep, cow, horse, dog, cat, rabbit, mouse, etc.), so it can be used as the agent for prevention and/or treatment of disease in which LPA takes part, for example, urinary disease, central nervous disease, inflammatory disease, circulatory disease, cancer, diabetes, immune system disorder or alimentary disease.

The compound, the salt thereof, the solvate thereof or the prodrug thereof obtained by using the method of screening of the present invention or the screening kit of the present invention is especially useful for prevention and/or treatment of urinary disease. LPA receptor agonist contracts urethra, so it is useful for prevention and/or treatment of urinary incontinence (e.g., stress incontinence, dementia incontinence, neurogenic incontinence, overflow incontinence, urgency incontinence, total incontinence, functional incontinence, and the like). LPA receptor antagonist makes urethra relax, and suppresses contriction of urethra and prostate, so it is useful for prevention and/or treatment of dysuria (e.g., hesitency, prolongation, decreased urinary stream, intermittent urination, two-phase micturition, and the like), ischuria, strage symptom such as pollakiuria, nocturia, furthermore, urodynia due to symptoms of infections such as cholera. Also, it makes urethra and prostate relax, so it is useful for prevention and/or treatment of benign prostatic hyperplasia.

"The disease in which LPA takes part" is not limited thereto, and it includes all diseases in which LPA takes part establishment, increment and/or continuation, and one in which the participation of LPA will be found in future.

Also, the antibody against the highly active LPA of the present invention, especially the one which is a neutralizing antibody, can inactivate signal transduction in which highly active LPA and/or LPA receptor takes part, such as cell stimulation activity via LPA receptor protein (e.g., accelerating or suppressing activity of release of arachidonic acid, release of acetylcholine, increase of intracellular calcium ion concentration, production of intracellular cyclic AMP (cAMP), production of intracellular cyclic GMP (cGMP), production of inositol phosphate, change in cell membrane potential, phosphorylation of intracellular protein, activation of c-fos, decrease of pH, and the like). So, besides the usage as the above-mentioned diagnostic product, it can be used, in the form of humanized antibody, as the agent for prevention and/or treatment of above-mentioned disease in which LPA takes part in mammals (for example, human or non-human animals such as monkey, sheep, cow, horse, dog, cat, rabbit, mouse, etc.), as well as the compound, the salt thereof, the solvate thereof or the prodrug thereof obtained by using the method of screening of the present invention or the screening kit of the present invention. In order to use the highly active LPA of the present invention as a medical drug, it can be used according to the prescription of general antibody drug.

For the purpose above described, the compound derived from the present invention, the salt thereof, the solvate thereof or the prodrug thereof may be normally administered systemically or locally, usually by oral or parenteral administration.

The doses to be administered are determined depending upon, for example, ages, body weights, symptoms, the desired therapeutic effects, the route of administration and the duration of the treatment. For the human adult, the doses per person are generally from 1 mg to 1000 mg, by oral administration, up to several times per day, and from 1 mg to 100 mg, by parenteral administration, up to several times per day, or continuous administration 1 to 24 hours per day from vein.

As mentioned above, the doses to be used depend upon various conditions. Therefore, there are cases in which doses lower than or greater than the ranges specified above may be used.

The compound derived from the present invention may be safely administered orally or parenterally (e.g. local, rectal, intravenous administration) alone or by mixing with a pharmaceutically acceptable carrier to be made into a pharmaceutical preparation, for example, solid agents for oral administration (for example, tablets including those coated with sugar or film, powders, pills, granules, capsules, etc.), liquid agents for oral administration, injections, suppositories, sustained release drugs, etc., in accordance with a known method generally used as a manufacturing method of a pharmaceutical preparation. The amount of the compound derived from the present invention in such preparations is about 0.01% of part weight to about 100% of part weight, preferably about 0.1% of part weight to about 50% of part weight, and more preferably, about 0.5% of part weight to about 20% of part weight, relative to the whole of the preparation.

The compound derived from the present invention used in the production of those pharmaceutical preparations is not limited to substantially pure and single substance, and may include impurities (e.g. by-product, solvent, raw material, or resolvent etc. which is derived from the production steps) as far as they are pharmaceutically acceptable as pharmaceutical bulk.

The carrier which is used in the production of the pharmaceutical preparation includes various conventional organic or inorganic carrier materials, such as vehicles, lubricants, binders and disintegrants of solid preparation, or solvents, solution adjuvants, suspending or emulsifying agents, tonicity agent, buffering agents and soothing agents, etc. of liquid preparation. If necessary, conventional preservatives, antioxidants, coloring agents, sweetening agents, absorbents, humectants can be used appropriately on adequate dose.

Solid agents for oral administration include tablets, pills, capsules, powders and granules. Capsules include hard capsules and soft capsules. In such solid agents, one or more of the active compound(s) may be alone, or admixed with vehicles (such as lactose, mannitol, glucose, microcrystalline cellulose, starch, corn starch, light anhydrous silicic acid, etc.), binders (such as hydroxypropyl cellulose, polyvinylpyrrolidone, magnesium metasilicate aluminate, crystalline cellulose, white sugar, D-mannitol, dextrin, hydroxypropylmethyl cellulose, starch, sucrose, gelatin, methylcellulose, sodium carboxymethyl cellulose, etc.), disintegrants (such as cellulose calcium glycolate, starch, carboxymethyl cellulose, carboxymethyl cellulose calcium, sodium carboxymethyl starch, L-hydroxypropyl cellulose, etc.), lubricants (such as magnesium stearate, calcium stearate, tarc, colloidal silica, etc.), and formulated according to common methods. The solid agents may, if desired, be coated with coating agents (such as white sugar, gelatin, hydroxypropyl cellulose or hydroxypropylmethyl cellulose phthalate), or be coated with two or more films. And further, coating may include containment within capsules of absorbable materials such as gelatin.

Liquid agents for oral administration include pharmaceutically acceptable solutions, suspensions, emulsions, syrups, elixirs, etc. In such liquid agents, one or more of the active compound(s) may be dissolved, suspended or emulsified into diluent(s) commonly used in the art (such as purified water, ethanol or a mixture thereof). The liquid agents may further comprise some additives, such as wetting agents, suspending agents, emulsifying agents, sweetening agents, flavoring agents, aroma, preservatives or buffering agents.

Injections for parenteral administration include any types of injections including drops. Examples of injections include intramuscular injections, subcutaneous injections, intradermal injections, intraarterial injections, intravenous injections, intraabdominal injections, intraspinal injections, intravenous drips, etc. Injections for parenteral administration also include sterile aqueous, suspensions, emulsions and solid forms which are dissolved or suspended into solvent(s) for injection immediately before use. In injections, one or more of the active compound(s) may be dissolved, suspended or emulsified into solvent(s). Examples of the solvents include distilled water for injection, physiological saline, macrogol, vegetable oil (e.g. sesame-seed oil, corn oil, olive oil, etc.), propylene glycol, polyethylene glycol, alcohol such as ethanol, or a mixture thereof.

Injections may comprise some additives, such as stabilizing agents (e.g. D-sorbitol, D-mannitol, L-alanine, ascorbic acid, albumin, inositol, sodium gluconic acid, sodium thioglycolate, polyoxyethylene hardened castor oil, etc.), solution adjuvants (e.g. glutamic acid, aspartic acid, POLYSORBATE 80 (registered trade mark), polyethylene glycol, propylene glycol, D-mannitol, benzyl benzoate, ethanol, trisaminomethane, cholesterol, triethanolamine, sodium carbonate, sodium citrate, etc.), emulsifying agents or suspending agents (e.g. surface-active agents such as stearyltriethanolamine, sodium lauryl sulfate, laurylaminopropionic acid, lecithin, benzalkonium chloride, benzetonium chloride, glycerin monostearate, etc.; hydrophilic polymer such as polyvinyl alcohol, polyvinylpyrrolidone, sodium carboxymethylcellulose, methylcellulose, hydroxymethylcellulose, hydroxyethylcellulose, hydroxypropylcellulose, etc.; and the like), soothing agents (e.g. benzyl alcohol, etc.), tonicity agents (e.g. glucose, D-sorbitol, sodium chloride, glycerin, D-mannitol, etc.), buffering agents (e.g. phosphate, acetate, carbonate, citrate, etc.), preservatives (e.g. parahydroxybenzoate esters, chlorobutanol, benzylalcohol, phenethyl alcohol, dehydroacetate, sorbic acid, etc.), antioxidants (e.g. sulfite salt, ascorbic acid, $\alpha$-tocopherol, etc.), and the like. They may be sterilized at a final step, or may be prepared and compensated according to aseptic manipulations. They may also be manufactured into sterile solid agents, for example, freeze-dried products, which may be dissolved in sterile water or some other sterile diluent(s) for injection immediately before use. Freeze drying can be carried out by the known method. Generally, a preferable method is to dry by freezing at −25° C. or below, and then raising the temperature of a drying rack to 25° C. to 40° C., while holding the vacuum pressure of a dry warehouse at about 13.3 Pa or below.

The other preparations for parenteral administration include liquids for external use, ointments, liniments, insufflations, spray preparations, suppositories and pessaries for vaginal administration which comprise one or more of the active substance(s) and may be prepared by methods known per se. Spray preparations may comprise, in addition to a diluent used in general, a stabilizer such as sodium bisulfite and an isotonization buffer, for example, tonicity agents such as sodium chloride, sodium citrate or citric acid. The preparation process of spray preparation is described in detail in, for example, U.S. Pat. Nos. 2,868,691 and 3,095,355.

The compound derived from the present invention, the salt thereof, the solvate thereof, or the prodrug thereof may be administered as a combination drug(s) by combining with other drug(s) for the purpose of (1) supplementating and/or enhancing the preventive and/or treatment effect of the compound, (2) improving pharmacokinetics and absorption of the compound, and reducing the dose of the compound, and/or (3) reducing side effect of the compound.

In addition, the compound derived from the present invention may be combined and administered as a combination drug(s) for the purpose of (1) supplementing and/or enhancing the preventive and/or treatment effect of the other drugs to be combined (hereinafter, which may be abbreviated to a concomitant drug(s)), (2) improving pharmacokinetics and absorption of the concomitant drug(s), and reducing the dose of the concomitant drug(s), and/or (3) reducing side effect of the concomitant drug(s).

The combination drug(s) of the compound derived from the present invention, the salt thereof, the solvate thereof, or the prodrug thereof and a concomitant drug(s) may be administered as one combination preparation comprising these components, or may be administered separately. When they are administered separately as independent preparations, they may be administered simultaneously or with time lag. Administration with time lag includes the method of administering the compound derived from the present invention, the salt thereof, the solvate thereof, or the prodrug thereof before other drugs and vice versa, and each administration route may be the same or different. There is no limitation on a disease on which the combination drug(s) of the compound derived from the present invention, the salt thereof, the solvate thereof, or the prodrug thereof and a concomitant drug(s) have preventive and/or treatment effects, so long as the preventive and/or treatment effect of the compound derived from the present invention, the salt thereof, the solvate thereof, or the prodrug thereof is supplemented and/or enhanced in the disease, or the preventive and/or treatment effect of the concomitant drug(s) is supplemented and/or enhanced in the disease. There is no limitation on the weight ratio between the compound derived from the present invention, the salt thereof, the solvate thereof, or the prodrug thereof and the concomitant drug(s) in the combination drug(s) of the compound derived from the present invention, the salt thereof, the solvate thereof, or the prodrug thereof and the concomitant drug(s).

Furthermore, the concomitant drug(s) is not limited to a low molecular weight compound, and may be a macromolecule protein, polypeptide, polynucleotide (DNA, RNA, gene), antisense, decoy, antibody, vaccine and the like. The dosage of the concomitant drug(s) can be properly selected according to the clinical dosage. The compounding ratio of the compound derived from the present invention and the concomitant drug(s) can be properly selected by the age and body weight of the object, administration route, administration term, target disease, symptom, combination and the like. For example, the amount of the concomitant drug(s) may be used 0.01 parts by weight to 100 parts by weight relative to 1 part by weight of the compound derived from the present invention, the salt thereof, the solvate thereof, or the prodrug thereof. The concomitant drug(s) may be selected from the following same or different group(s) and administered in combination, if desired.

The concomitant drug(s) for supplementation and/or enhancement of the preventive and/or therapeutic effect of the compound derived from the present invention includes not only those which have so far been found but also those which will be found on the basis of the aforementioned mechanism. As previously described, the compound derived from the present invention, the salt thereof, the solvate thereof or the prodrug thereof includes the LPA receptor agonist or the LPA receptor antagonist, so the concomitant drug(s) which can be used in combination with the compounds of the present invention include, for example, those given below.

As concomitant drug(s) to complement and/or to enhance the preventing and/or treating effect of the LPA receptor agonist for urinary diseases, other treating agents for urinary diseases, for example, α1 agonists, β2 agonists and anticholinergic agents etc. are given. As α1 agonists, midodrine hydrochloride etc. are given. As β2 agonists, clenbuterol hydrochloride etc. are given. As anticholinergic agents, for example, oxybutynin hydrochloride, bethanechol chloride, propiverine hydrochloride, propantheline bromide, methylbenactyzium bromide, scopolamine butylbromide, tolterodine tanrate, trospium chloride, Z-338, UK-112166-04, KRP-197, darifenacin and YM-905 etc. are given.

As concomitant drug(s) to complement and/or to enhance the preventing and/or treating effect of the LPA receptor antagonist for urinary diseases, other treating agents for urinary diseases, for example, α1 antagonists, anticholinergic agents, 5α-reductase inhibitors and/or antiandrogen agent etc. are given. As α1 antagonists, terazosin hydrochloride, bunazosin hydrochloride, urapidil, tamsulosin hydrochloride, doxazosin mesilate, prazosin hydrochloride, indolamine, naftopidil, alfzosin hydrochloride, AIO-8507L and silodosin etc. are given. As anticholinergic agents, for example, oxybutynin hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin and YM-905 etc. are given. Anticholinergic agents are used only when such diseases are not associated with prostatomegaly. Mainly, they are used for pollakiuria and urinary incontinence that are not associated with prostatomegaly. As 5α-reductase inhibitors, for example, finasteride and GI-998745 etc. are given. As antiandrogen agent, for example, oxendolone, osaterone acetate and bicalutamide etc. are given.

The following excellent effects can be obtained by combining the compound derived from the present invention with the concomitant drug(s).

(1) The concomitant use can decrease the dose compared to administration alone of the compound derived from the present invention, the salt thereof, the solvate thereof, or the prodrug thereof, or the concomitant drug(s);

(2) The compound derived from the present invention and the concomitant drug(s) can be selected according to a patient's symptom (mild case, severe case etc.);

(3) The selection of the concomitant drug(s) of which mechanism of the action is different from that of the compound derived from the present invention can decrease the dose in patients and extend the therapeutic period;

(4) The selection of the concomitant drug(s) of which mechanism of the action is different from that of the compound derived from the present invention can maintain the therapeutic effect;

(5) The combination of the compound derived from the present invention with the concomitant drug(s) can obtain the synergistic effect.

Hereinafter, to use the compound derived from the present invention, the salt thereof, the solvate thereof, or the prodrug thereof in conjunction with a concomitant drug(s) is termed "the combination drug(s) of the present invention". In the case of using the combination drug(s) of the present invention, there is no particular limitation for administration time of the compound derived from the present invention, the salt thereof, the solvate thereof, or the prodrug thereof or a concomitant drug(s). The administration of the compound derived from the present invention, the salt thereof, the solvate thereof, or the prodrug thereof or pharmaceutical composition thereof and a concomitant drug(s) or pharmaceutical composition thereof to the administration object includes a simultaneous administration and administrations with time difference. The dose of a concomitant drug(s) can be properly selected according to the object of the administration, route of the administration, disease, combination, etc., as far as it conforms to the clinical dose. There is no particular limitation on the way of administration, as far as the compound derived from the present invention, the salt thereof, the solvate thereof, or the prodrug thereof and a concomitant drug(s) are combined in vivo. The way of administration includes, for example, (1) administration of a single preparation obtained by preparing the compound derived from the present invention, the salt thereof, the solvate thereof, or the prodrug thereof and a concomitant drug(s) simultaneously, (2) simultaneous administration of two kind of preparation obtained by preparing the compound derived from the present invention, the salt thereof, the solvate thereof, or the prodrug thereof and a concomitant drug(s) separately by the same route of administration, (3) administrations with time difference of two kind of preparation obtained by preparing the compound derived from the present invention, the salt thereof, the solvate thereof, or the prodrug thereof and a concomitant drug(s) separately by the same route of administration, (4) simultaneous administration of two kind of preparation obtained by preparing the compound derived from the present invention, the salt thereof, the solvate thereof, or the prodrug thereof and a concomitant drug(s) separately by different route of administration, (5) administrations with time difference of two kind of preparation obtained by preparing the compound derived from the present invention, the salt thereof, the solvate thereof, or the prodrug thereof and a concomitant drug(s) separately by different route of administration (such as administration in the order of the compound derived from the present invention, the salt thereof, the solvate thereof, or the prodrug thereof and a concomitant drug(s), or vice-versa, etc.

In the administration of the combination drug(s) of the present invention, the compound derived from the present invention, the salt thereof, the solvate thereof, or the prodrug thereof and/or the concomitant drug(s) can be safely administered as they are or after being mixed with a pharmaceutically acceptable carrier according to a per se known method usually employed in the production of pharmaceutical preparations, orally or parenterally (for example, topical administration, rectal administration, intravenous administration, etc.) in the form of solid preparations for internal use (e.g. tablets including sugar coated tablets and film-coating tablets), powders, pills, granules, capsules, etc.), liquid preparations for internal use, liquid preparations for external use, injections, suppositories, delayed-release preparations or the like.

The carrier which is used in the production of the pharmaceutical preparation includes various conventional organic or inorganic carrier materials, such as excipients, lubricants, binders and disintegrators for solid preparations, solvents, solubilizers, suspending or emulsifying agents, isotonic agents, buffers and soothing agents, etc. If necessary, conventional preservatives, antioxidants, coloring agents, sweetening agents, adsorbents, wetting agents, and the like can be used appropriately in a suitable amount.

The excipient includes, for example, lactose, mannitol, glucose, microcrystalline cellulose, starch, corn starch, light anhydrous silicic acid, and the like. The binder includes, for example, hydroxypropyl cellulose, polyvinylpyrrolidone, magnesium metasilicate aluminate, crystalline cellulose, white soft sugar, D-mannitol, dextrin, hydroxypropylmethyl cellulose, starch, sucrose, gelatin, methylcellulose, sodium carboxymethylcellulose, and the like. The disintegrator includes, for example, cellulose calcium glycolate, starch, carboxymethylcellulose, carboxymethylcellulose calcium, sodium carboxymethylstarch, L-hydroxypropyl cellulose, and the like. The lubricant includes, for example, magnesium stearate, calcium stearate, talk, colloid silica and the like. The solvent medium includes, for example, distilled water for injection, physiological saline solution, macrogol, vegetable oil (such as sesame oil, corn oil, olive oil), alcohols (e.g. propylene glycol, polyethylene glycol, ethanol, etc.) or a mixture thereof. The stabilizer includes, for example, D-sorbitol, D-mannitol, L-alanine, ascorbic acid, albumin, inositol, sodium gluconate, sodium thioglycolate, polyoxyethylene hardened caster oil, etc. The solubilizer includes, for example, glutamic acid, aspartic acid, Polysolbate 80 (trade name), polyethylene glycol, propylene glycol, D-mannitol, benzyl benzoate, ethanol, trisaminomethane, cholesterol, triethanolamine, sodium carbonate, citric sodium, etc. The emulsifying or suspending agent includes, for example, surfactants (for example, stearyl triethanolamine, sodium lauryl sulfate, laurylaminopropionate, lecithin, benzalkonium chloride, benzethonium chloride, glyceryl monostearate, etc.), hydrophilic polymers (for example, polyvinyl alcohol, polyvinylpyrrolidone, sodium carboxymethylcellulose, methylcellulose, hydroxymethylcellulose, hydroxyethylcellulose, hydroxypropylcellulose etc.) and the like. The soothing agents include, for example, benzyl alcohol, and the like. The isotonic agents include, for example, glucose, D-sorbitol, sodium chloride, glycerin, D-mannitol, and the like. The buffers include, for example, a buffer solution of phosphates, acetates, carbonates, citrates, or the like. The preservative includes, for example, p-hydroxybenzoic acid ester, chlorobutanol, benzyl alcohol, phenethyl alcohol, dehydroacetic acid, sorbic acid, and the like. The antioxidant includes, for example, sulfites, ascorbic acid, α-tocopherol, and the like.

The compounding ratio of the compound derived from the present invention, the salt thereof, the solvate thereof, or the prodrug thereof in the combination drug(s) of the present invention varies depending on the dosage form. It is usually about 0.01% by weight to 100% by weight relative to the whole preparation, preferably about 0.1% by weight to 50% by weight relative to the whole preparation, more preferably about 0.5% by weight to 20% by weight relative to the whole preparation.

The compounding ratio of the concomitant drug(s) in the combination drug(s) of the present invention varies depending on the dosage form. It is usually about 0.01% by weight to 100% by weight, preferably about 0.1% by weight to 50% by weight relative to the whole preparation, more preferably about 0.5% by weight to 20% by weight relative to the whole preparation.

The content of the additive such as carrier, etc. in the combination drug(s) of the present invention varies depending on the dosage form. It is usually about 1% by weight to 99.99% by weight, preferably about 10% by weight to 90% by weight relative to the whole preparation. In addition, it may be the same in the formulation of the compound derived from the present invention, the salt thereof, the solvate thereof, or the prodrug thereof and the concomitant drug(s) independently.

These drug preparations can be prepared by the usual method (such as the method described in Japanese Pharmacopoeia, etc.). The tablet can be prepared by mixing drug(s) uniformly in the presence or absence of excipients, disintegrators, or other appropriate additives to prepare granulated powder in an appropriate manner, and then compacting with a lubricant, etc.; by mixing drug(s) uniformly in the presence or absence of excipients, disintegrators, or other appropriate additives in an appropriate manner, and then compacting the mixture directly; or by optionally adding an appropriate additive to previously granulated powder, mixing the mixture uniformly and then compacting into tablets. If necessary, the tablet may be prepared with coloring agents, flavoring substance, etc. Furthermore, it can be coated by using appropriate coating agents. The injection preparation can be prepared by the following method. A certain amount of the drug(s) is dissolved, suspended or emulsified usually in an aqueous medium such as distilled water for injection, physiological saline solution, and Ringer solution, or in a non-aqueous medium such as vegetable oil, etc.; or a certain amount of the drug(s) is sealed in a container for injection. The carrier for the preparation for oral administration includes a conventional material used in the field of pharmaceutical formulation, such as starch, mannitol, crystalline cellulose, sodium carboxymethylcellulose, etc. The carrier for injections includes, for example, distilled water, physiological saline solution, glucose solution, infusion, and the like. If necessary, additives used in the drug product in general can be added in addition.

Although the dose of the combination drug(s) of the present invention depends on the age, weight, disease symptom, therapeutic effect, administration route, therapy period, and the like, the compound derived from the present invention, the salt thereof, the solvate thereof, or the prodrug thereof and the concomitant drug(s) are usually administered orally once or several times per day at a dose per administration of from 0.1 mg to 1000 mg per human adult, or parenterally (preferably intravenous administration once or several times per day at a dose per administration of from 0.1 mg to 100 mg per human adult, or continuously administered intravenously for 1 hour to 24 hours per day.

It goes without saying that the dose of these compounds may be less than the aforementioned value or may need to exceed the aforementioned range because the dose varies under various conditions as mentioned above. The concomitant drug(s) can be administrated at arbitrary dose as far as the side effect is not a serious problem and the purpose of the present invention can be achieved. The daily dose as a concomitant drug(s) differs depending on age, sex, body weight, different sensitivity, time and interval of administration object, characteristics of pharmaceutical preparation, dispensing, kind, and type of active ingredient of medicinal preparation; and the like, so that it is not particularly limited.

In the mode of administration of the combination drug(s) of the present invention, the compounds may be administered simultaneously, or the concomitant drug(s) may be administered firstly followed by administering the compound derived from the present invention, the salt thereof, the solvate thereof, or the prodrug thereof, or the compound derived from the present invention, the salt thereof, the solvate thereof, or the prodrug thereof may be administered firstly, followed by administering the concomitant drug(s). In the case of time difference administration, time difference differs depending on active ingredient to be administered, dosage form, and administration route. For example, in the case where the concomitant drug(s) may be administered firstly, the compound derived from the present invention, the salt thereof, the solvate thereof, or the prodrug thereof can be administered within 1 minute to 3 days, preferably 10 minutes to 1 day, more preferably 15 minutes to 1 hour after the administration of the concomitant drug(s).

In the case where the compound derived from the present invention, the salt thereof, the solvate thereof, or the prodrug thereof is administered firstly, the concomitant drug(s) can be administered within 1 minute to 1 day, preferably 10 minutes to 6 hours, more preferably 15 minutes to 1 hour after the administration of the compound derived from the present invention, the salt thereof, the solvate thereof, or the prodrug thereof, and the like.

Pharmacological Activity:

As the method of screening of the present invention, for example, the following method can be cited. It is able to discover the agonist or the antagonist of the LPA receptor by the following method of screening. Though the following method discloses the method using EDG-2 as the LPA receptor, other LPA receptor may be used in the same way.

Evaluation of the Activity of EDG-2 Agonist or Antagonist:

For example, the action against EDG-2 is evaluated by the following experimental test.

It is able to evaluate the activity of EDG-2 agonist or antagonist by using Chinese Hamster Ovary (CHO) cells that overexpresses human EDG-2 gene.

EDG-2 expressing cells are cultured using 10% FBS (fetal bovine serum), penicillin/streptomycin, and blasticidin (5 μg/mL)—containing Ham's F12 medium (manufactured by Gibco). Firstly, in order to incorporate Fura2-AM (manufactured by Dojindo) intracellular, cells are incubated in Fura-2 AM solution [10% FBS, HEPES buffer (20 mM, pH 7.4), probenecid (2.5 mM, manufactured by Sigma (No P-8761))—containing Ham's F12 medium] (5 μM) for 60 minutes at 37° C. and are washed once with Hanks solution which contains HEPES buffer (20 mM, pH 7.4) and probenecid (2.5 mM), and are immersed into the Hanks solution in sequence. Continuously, it is able to evaluate according to following the method (1) or (2).

(i) Evaluation of Antagonistic Activity

Plates are set in fluorescent drug screening system (manufactured by Hamamatsu Photonics Company) and intracellular calcium ion concentration is measured for 30 seconds with no stimulation and then solution of the test compound is added. Five minutes after adding thereto the highly active LPA (final concentration: 100 nM) is added, the increase of intracellular calcium ion concentrations before and after the addition of the highly active LPA are measured every 3 seconds. The compound is dissolved in DMSO, and it is added so that the final concentration become 1 nM to 10 μM. EDG-2 antagonistic activity is calculated as an inhibition rate (%) by the equation {Inhibition rate (%)=[(A−B)/A]×100}, wherein the peak value of the highly active LPA (final concentration: 100 nM) in a well into which DMSO containing no compound is added is regarded as a control value (A), and in the cells treated with the compound the difference (B) between the value before addition of the highly active LPA and that after the addition is obtained and compared with the control value. The $IC_{50}$ value is calculated as a concentration of the compound to be tested which showed 50% inhibition.

(ii) Evaluation of Agonistic Activity

Plates are set in above-mentioned fluorescent drug screening system and measured for 30 seconds with no stimulation and then solution of the test compound is added. The compound to be evaluated is dissolved in DMSO and the like and it is added so that the final concentration become 0.1 nM to 10 μM and the final concentration of DMSO become to be ¹/₁₀₀₀. Intracellular calcium ion ($Ca^{2+}$) concentration (Fura2-$Ca^{2+}$) before and after the addition are measured every 3 seconds (excitation wave length: 340 nm and 380 nm; fluorescent wave length: 500 nm).

EDG-2 agonistic activity is calculated as an increasing rate (%) by the equation {Increasing rate (%)=B−A)×100}, wherein the peak value of the LPA (e.g., 18:3-LPA and the like) or the highly active LPA in a well into which DMSO instead of test compound is added is regarded as a control value (A), and in the cells treated with the compound the difference (B) between the value before addition of the test compound and that after the addition is obtained and compared with the control value. The $EC_{50}$ value is calculated by increasing rate (%) of test compound in various concentration.

Effect of the Invention:

By the present invention, a preventive and/or therapeutic substance for diseases in which LPA takes part can be obtained effectively. The method of screening of the present invention is different from conventional method of using LPA, and is the method of screening which reflects in vivo environment of disease by reason of using the highly active LPA which is a causative agent of various diseases as ligand.

BEST MODE FOR CARRYING OUT THE INVENTION

Figure 1:
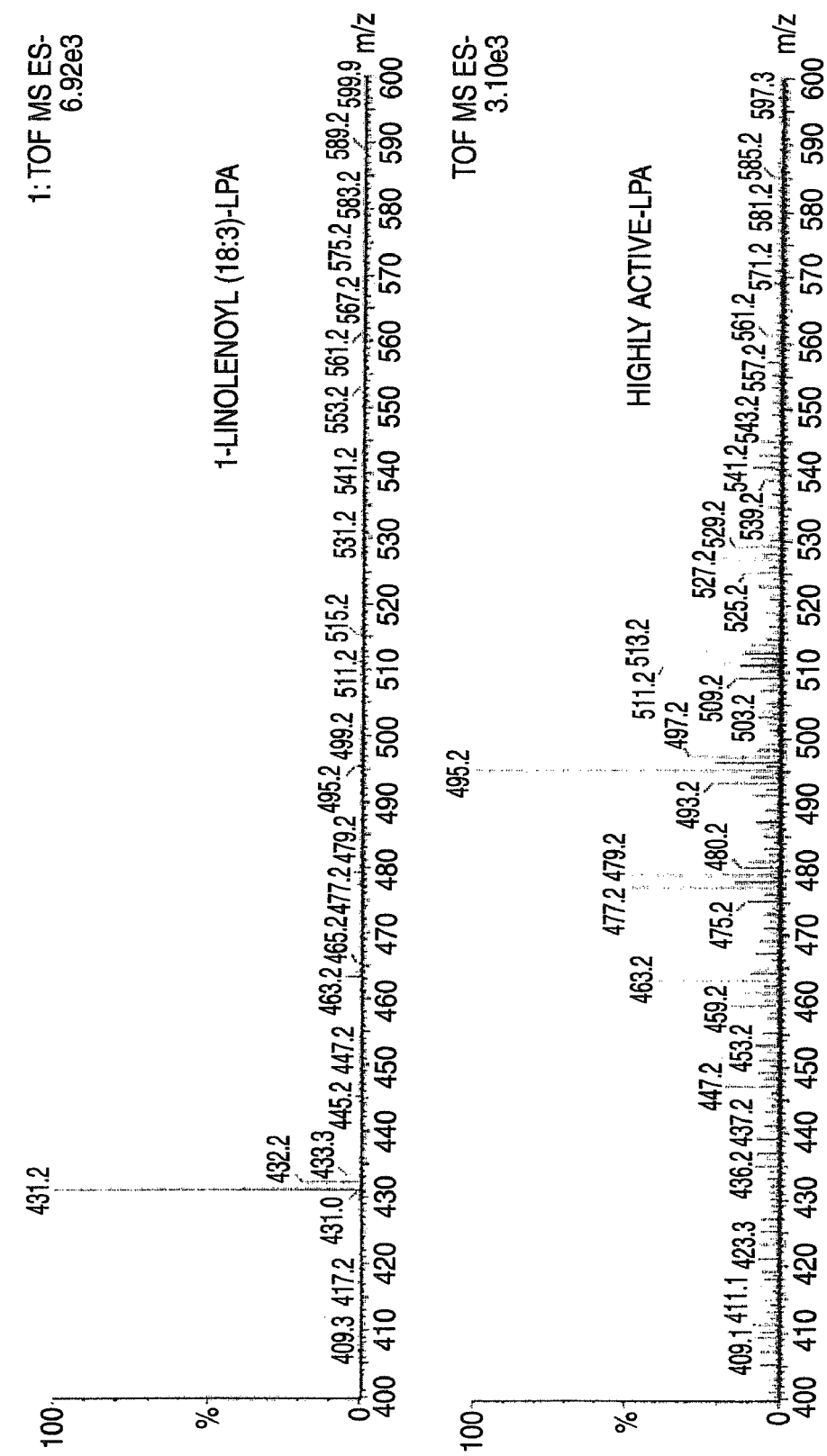
FIG. 1 shows Mass spectrometry data of (1) 1-linolenoyl (18:3)-LPA and (2) highly active LPA obtained by oxidation of it.

Hereinafter, Reference Examples and Examples are disclosed, but the present invention is not limited thereto. And it may be changed within the scope of the present invention.

It was confirmed by the following experiment that the LPA which was oxidized functions as the highly active LPA.

As the entire manipulations, the methods of the common procedure based on a basic biological technique were used. And with regard to a measuring method for evaluating the following improvement was done for an object of improving the measuring precision and/or measuring sensitivity. Detailed experimental methods will be shown as hereunder.

REFERENCE EXAMPLE 1

Preparation of (2S)-2-hydroxy-3-(phosphonooxy) propyl (9Z, 12Z, 15Z)-9,12,15-octadecatrienoate (hereinafter referred to as "1-linolenoyl(18:3)-LPA")

(i) Preparation of 18:3-lysophosphatidylcholine (LPC) from 18:3-phosphatidylcholine (PC) using phospholipase $A_2$ ($PLA_2$)

18:3-PC (Avanti, 850395C) was dissolved in mixed solvent of diethyl ether and methanol (diethyl ether: methanol=85: 15) at the concentration of 50 mg/mL. To this solution, $PLA_2$ (Sigma, P-9279) (400 U/mL in 10 mM Tris-HCl (pH 7.4)) was added under stirring at the ratio of 0.48 U of $PLA_2$ per 1 mg of 18:3-PC (final 2.4 U $PLA_2$/mg 18:3-PC). The solution was concentrated under the reduced pressure. The residue was dissolved in chloroform and the solution was dispensed into the centrifugation tube. After centrifugation (1200 rpm, 3 min, room temperature), the supernatant was concentrated under the reduced pressure. The residue was dissolved in methanol and 20-fold of diethyl ether. The mixed solution was stirred at room temperature and centrifuged as described above to precipitate 18:3-LPC.

(ii) Preparation of 18:3-lysophosphatidic acid (LPA) from 18:3-lysophosphatidylcholine (LPC) using phospholipase D (PLD)

To the reaction solvent (40 mL, 5 mM sodium fluoride, 200 mM Tris-HCl (pH 7.4)), 18:3-LPC (0.60 g) was dissolved. To the reaction solution, PLD (1000 U/mL) was added (final concentration: 333 U/mL) under stirring vigorously. Reaction was conducted overnight, and complete disintegration of LPC was confirmed by TLC. The pH of reaction solution was adjusted to about 2 to 3 by addition of 6 N hydrochloric acid. The reaction solution was extracted with chloroform several times. Each organic layer was neutralized by addition of 28% aqueous ammonia. It was confirmed by TLC that no LPA exists in aqueous layer, then organic layer was combined and concentrated under the reduced pressure. Concentrated LPA was dissolved in mixed solvent of chloroform and methanol (chloroform : methanol=70:30), and purified partially with silica gel column (wakogel C-200). Then, purification by HPLC with reversed phase column (C18) was conducted to give the title compound, 1-linolenoyl(18:3)-LPA, having the following physical data.

<TLC data>

TLC: Rf 0.54 (chloroform:methanol:water=65:35:5);

<NMR data>

NMR (DMSO-$d_6$): δ 0.91 (t, J=7.5 Hz, 3H, C1), 1.28 (m, 8H, C12, C13, C14, C15), 1.50 (m, 2H, C16), 2.03 (m, 4H, C2, C11), 2.27 (t, J=7.5 Hz, 2H, C17), 2.76 (t, J=6.0 Hz, 4H,

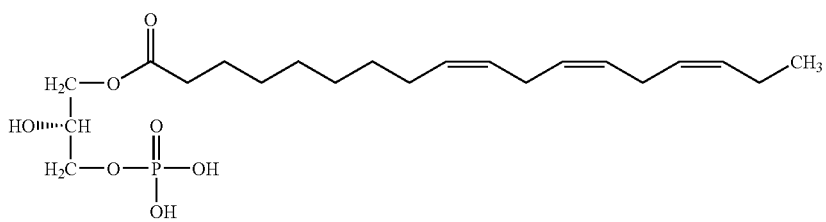

C5, C8), 3.67 (m, 3H, C20, C21), 3.92 (m, 2H, C19), 5.31 (m, 6H, C3, C4, C6, C7, C9, C10).

EXAMPLE 1

Preparation of Highly Active LPA from 1-linolenoyl(18:3)-LPA:

To the mixed solution (0.9 mL) of acetonitrile and methanol (acetonitrile: methanol=1:2) containing 1-linolenoyl(18:3)-LPA (1.0 mg) obtained in Reference Example 1, the mixed solution (0.1 mL) of acetonitrile and methanol (acetonitrile: methanol=1:2) containing m-chloro perbenzoic acid (4.2 mg) was added and stirred. After incubation for 16 hours at room temperature, the reaction mixture was concentrated and the residue was dissolved into the mixed solution (1.6 mL) of chloroform and methanol (chloroform:methanol=9.7:1). The reaction mixture was purified by silica gel column chromatography (Sep-Pak Vac Silica 6 cc (500 mg), chloroform: methanol=1:0 to 0:1) to give the highly active LPA having following the physical data.

<Mass Spectrum Data>
$O_3$-18:5-LPA HRMS (Q-TOF-ESI Neg.) (m/z): [M−H]$^-$ calcd for $C_{21}H_{32}O_{10}P$ 475.1733, found 475.1756; $O_3$-18:4-LPA HRMS (Q-TOF-ESI Neg.) (m/z): [M−H]$^-$ calcd for $C_{21}H_{34}O_{10}P$ 477.1890, found 477.1911; $O_3$-18:3-LPA HRMS (Q-TOF-ESI Neg.) (m/z): [M−H]$^-$ calcd for $C_{21}H_{36}O_{10}P$ 479.2046, found 479.2033; $O_4$-18:3-LPA HRMS (Q-TOF-ESI Neg.) (m/z): [M−M]$^-$ calcd for $C_{21}H_{36}O_{11}P$ 495.1995, found 495.1996; $O_4$-18:2-LPA HRMS (Q-TOF-ESI Neg.) (m/z): [M−H]$^-$ calcd for $C_{21}H_{38}O_{11}P$ 497.2152, found 497.2148.

EXAMPLE 1-1

Preparation of Highly Active LPA from 1-linoleoyl(18:2)-LPA

By the same procedure as described in Example 1 using D(+)-sn-1-o-linoleoyl-glyceryl-3-phosphate. sodium salt (echeon, L-0182) instead of 1-linolenoyl(18:3)-LPA, the highly active LPA, (2S)-2-hydroxy-3-[8-{(2R,3S)-3-[((2R,3S)-3-pentyl-2-oxiranyl)methyl]-2-oxiranyl}octanoyloxy]propyl phosphate

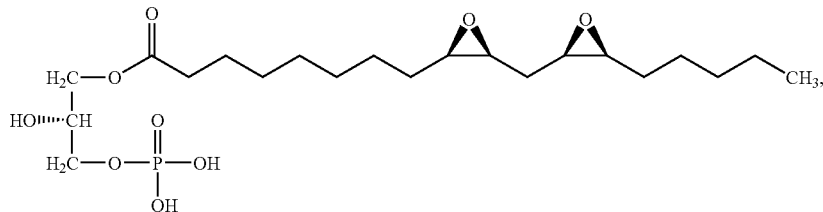

(2S)-2-hydroxy-3-[8-{(2S,3R)-3-[((2S,3R)-3-pentyl-2-oxiranyl)methyl]-2-oxiranyl}octanoyloxy]propyl phosphate

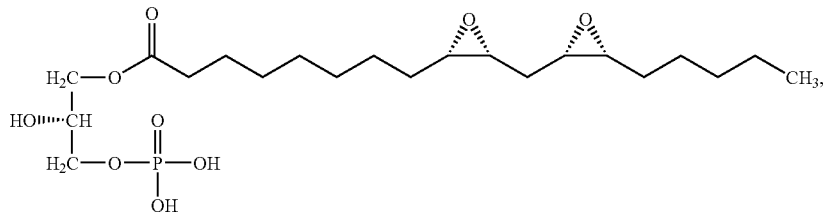

(2S)-2-hydroxy-3-[8-{(2R,3S)-3-[((2S,3R)-3-pentyl-2-oxiranyl)methyl]-2-oxiranyl}octanoyloxy]propyl phosphate

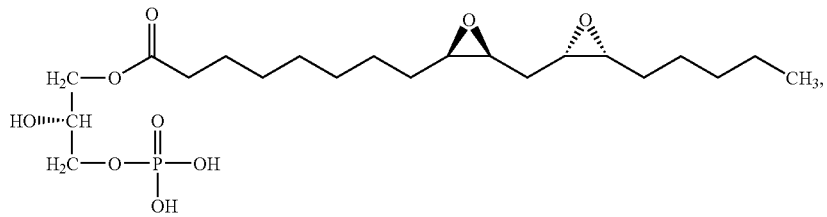

and/or (2S)-2-hydroxy-3-[8-{(2S,3R)-3-[((2R,3S)-3-pentyl-2-oxiranyl)methyl]-2-oxiranyl}octanoyloxy]propyl phosphate

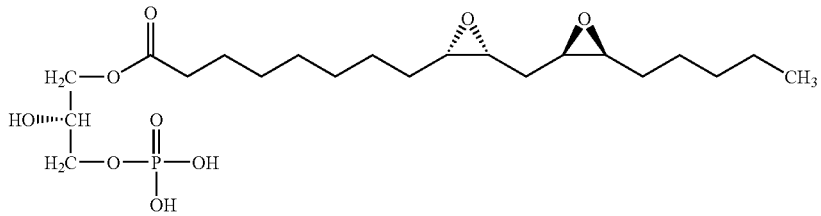

having the following physical data were obtained.

<Mass Spectrum Data>
HRMS (Q-Tof-ESI Neg.) (m/z): [M–H]⁻ calcd for $C_{21}H_{38}O_9P$ 465.2254, found 465.2288; HRMSMS (Q-Tof-ESI Neg.) (m/z): [M–H]⁻—$C_3H_7O_5P$ 311.2368, [M–H]⁻—$C_3H_7O_5P$—$H_2O$ 293.2284, [M–H]⁻—$C_{18}H_{30}O_3$ 171.0207, [M–H]⁻—$C_{18}H_{30}O_3$—$H_2O$ 153.0045;

<NMR Data>
NMR (deuterium oxide): δ 0.8 (t, J=7.2 Hz, 3H), 1.2-1.6 (m, 20H), 1.6 (dt, J=15.0, 7.5 Hz, 0.5H), 1.8 (t, J=6.4 Hz, 1H), 2.0 (td, J=14.9, 5.0 Hz, 0.5H), 2.3 (t, J=7.5 Hz, 1H), 3.1-3.2 (m, 2H), 3.2-3.3 (m, 2H), 3.7-3.9 (m, 2H), 4.0 (m, 1H), 4.1 (dd, J=11.5, 6.6 Hz, 1H), 4.1 (dd, J=11.5, 3.7 Hz, 1H).

EXAMPLE 1-2

Preparation of Highly Active LPA from 1-archidonoyl(20:4)-LPA

By the same procedure as described in Example 1, using D(+)-sn-1-o-arachidonoyl-glyceryl-3-phosphate. sodium salt (echeon, L-0204) instead of 1-linolenoyl(18:3)-LPA, The highly active LPA having the following physical data was obtained.

<Mass Spectrum Data>
$O_1$-20:4-LPA HRMS (Q-Tof-ESI Neg.) (m/z): [M–H]⁻ calcd for $C_{23}H_{38}O_8P$ 473.2304, found 473.2289; $O_2$-20:4-LPA HRMS (Q-Tof-ESI Neg.) (m/z): [M–H]⁻ calcd for $C_{23}H_{38}O_9P$ 489.2253, found 489.2218; $O_3$-20:6-LPA HRMS (Q-Tof-ESI Neg.) (m/z): [M–H]⁻ calcd for $C_{23}H_{34}O_{10}P$ 501.1890, found 501.1871; $O_3$-20:5-LPA HRMS (Q-Tof-ESI Neg.) (m/z): [M–H]⁻ calcd for $C_{23}H_{36}O_{10}P$ 503.2046, found 503.2010; $O_3$-20:4-LPA HRMS (Q-Tof-ESI Neg.) (m/z): [M–H]⁻ calcd for $C_{23}H_{38}O_{10}P$ 505.2203, found 505.2168; $O_4$-20:5-LPA HRMS (Q-Tof-ESI Neg.) (m/z): [M–H]⁻ calcd for $C_{23}H_{36}O_{11}P$ 519.1995, found 519.1980; $O_4$-20:4-LPA HRMS (Q-Tof-ESI Neg.) (m/z): [M–H]⁻ calcd for $C_{23}H_{38}O_{11}P$ 521.2152, found 521.2133; $O_5$-20:5-LPA HRMS (Q-Tof-ESI Neg.) (m/z): [M–H]⁻ calcd for $C_{23}H_{36}O_{12}P$ 535.1944, found 535.1973; $O_5$-20:4-LPA HRMS (Q-Tof-ESI Neg.) (m/z): [M–H]⁻ calcd for $C_{23}H_{38}O_{12}P$ 537.2101, found 537.2099.

EXAMPLE 2

Comparing by Mass Spectrometry:

It was confirmed by mass spectrometry that the highly active LPA obtained in Example 1 is different from 1-linolenoyl(18:3)-LPA obtained in Reference Example 1. Hereinafter, condition for measuring and procedure are described.

<Material>
silica gel column:Develosil 60-5 (2.0 mm×150 mm) (Nomura Chemical Co., Ltd.) pre column: 1.5 mm×10 mm guard column (Nomura Chemical Co., Ltd.)

<Prepared Reagent>
HPLC Elution Buffer
(1) Buffer A: 0.1% ammonium formate (pH 6.4)/acetonitrile-methanol mixed solvent (acetonitrile:methanol=1:1)
(2) Buffer B: 0.1% ammonium formate (pH 6.4)/methanol-water mixed solvent (methanol:water=2:1)

<Instrument>
(1) HPLC (Waters, Alliance 2795)
(2) Q-TOF mass spectrometry (Micromass, Q-TOF Ultima API)

<Procedure>
(1) Detection of 1-linolenoyl(18:3)-LPA using LC/ESI-TOF-MS
Measurement was conducted by using above-mentioned apparatus with following conditions of HPLC and mass spectrometry.
ESI-MS Negative Ion Mode

[Sourse]
Capillary: 2.9; Cone: 40; RF Lens1:50.0; Sourse Temp (° C.): 100; Desolvation Temp (° C.): 200; Conc Gas Flow (L/Hr): 50; Desolvation Gas Flow (L/Hr): 800

[MS]
LM Resolution: 10.0; HM Resolution: 10.0; Collision Energy: 5.0

[MS2] TOF (kV): 9.10; MCP: 2000

[LC]
HPLC Gradient:ratio (%) of Buffer A and Buffer B is shown in parentheses ( ). 0 min (100:0); 5 min (100:0); 20 min (70:30); 30 min (70:30); 35 min (100:0) Flow Rate: 0.2 mL/min Injection Vol.: 30 μL (100 μg/mL 1-linoleoyl(18:3)-LPA)

(2) Detection of Highly Active LPA Using LC/ESI-TOF-MS
The highly active LPA (2 μL) obtained in Example 1 was diluted (500-fold) with mixed solvent of acetonitrile and methanol (acetonitrile : methanol=1:2) and directly injected to above-mentioned apparatus. Measurement was conducted with following condition of mass spectrometry.
ESI-MS Negative Ion Mode

[Sourse]
Capillary: 2.9; Cone: 40; RF LensI: 50.0; Sourse Temp (° C.): 100; Desolvation Temp (° C.): 200; Cone Gas Flow (L/Hr): 50; Desolvation Gas Flow (L/Hr): 800

[MS]
LM Resolution: 15.0; HM Resolution: 15.0; Collision Energy: 5.0

[MS2]
TOF (kV): 9.10; MCP: 2000

<Result>

The highly active LPA obtained in Example 1 was different from 1-linolenoyl(18:3)-LPA obtained in Reference Example 1 in spectrum chart of mass spectrometry (FIG. 1).

EXAMPLE 3

Confirmation of Pharmacological Activity and Comparing Activity with LPA (1) Evaluation in [Ca$^{2+}$]i Assay System The agonistic activity to the receptor was evaluated by using human EDG-2 gene—over expressed Chinese Hamster Ovary (CHO) cells. EDG-2 expressed cells were cultured in Ham's F12 medium (manufactured by Gibco BRL) containing 10% FBS (fetal bovine serum), penicillin/streptomycin and blasticidin (5 μg/mL). Firstly, the cells were incubated in a Fura2-AM solution [Ham's F12 medium containing 10% FBS, HEPFS buffer (20 mM, pH 7.4), probenecid (2.5 mM) (manufactured by Sigma, P-8761)] at 37° C. for 60 minutes to load Fura2-AM (Dojindo) into the cell. The cells were washed once with a Hanks solution containing HEPES buffer (20 mM, pH 7.4) and probenecid (2.5 mM) and immersed in the Hanks solution. The plate was set on fluorescent drug screening system (manufactured by Hamamatsu photonics) and measured for 30 seconds without stimulation. The solution of the highly active LPA obtained in Example 1 was added thereto. The highly active LPA was dissolved in saline and added to give a final concentration of 0.1 nM to 10 μM. The intracellular Ca$^{2+}$ concentration (Fura2-Ca$^{2+}$ fluorescence) was measured before and after addition of the highly active LPA every 3 seconds (excitation wavelength 340 nm and 380 nm, emission wavelength 500 nm).

<Result>

The highly active LPA obtained in Example 1 was revealed that it has an increasing effect on concentration of intracellular calcium of EDG-2 expressing cell.

(2) Evaluation in Contraction-measuring System Using an Isolated Urethra of Rat

After sacrificing female or male CD (SD) IGS rats (Charles River Japan Inc., 8-9 week-old in use) by blowing heads and exsanguinating from carotid artery and jugular vein, urethra under pubis was isolated carefully and soaked in Krebs-Henseleit solution (112 mM NaCl, 5.9 mM KCl, 2.0 mM CaCl$_2$, 1.2 mM MgCl$_2$, 1.2 mM NaH$_2$PO$_4$, 25.0 mM NaHCO$_3$, 11.5 mM Glucose) immediately. Urethra part was cut from isolated sample, and was dissected flatly and subsequently was cut parallel to circular muscle. Thus, 2-3 strips of sample that are 3-4 mm long by 2-3 mm wide were made from one animal.

The made samples were suspended in the Magnus tube (volume: 10 mL) filled by Krebs-Henseleit solution (vented by 37±1° C., mixed gas [95% O$_2$+5% CO$_2$]). The samples were added about 0.5 g tension and stabilized for 60 min, and subsequently the contractile activity was recorded on recorder (lincarcoder WR3320: GRAPHTEC CORP.) via a pressure amplifier (AP-621G: Nihon Kohden Ltd) from Force displacement transducer (FD pick-up TB-611T; Nihon Kohden Ltd).

The contractile reaction of control was given by stimulation of high concentration KCl solution (solution replaced all NaCl with KCl). By the addition of the highly active LPA prepared in Example 1, Example 1-1 or Example 1-2, dose-dependency of urethra contraction was measured.

<Result>

The highly active LPA obtained in Example 1, Example 1-1 and Example 1-2 were revealed that they have a contracting effect on the isolated urethra of rat.

(3) Evaluation in the Increasing Urethral Pressure Measuring System Under Anesthesia of Rat with Urethane Male CD (SD) IGS rats (Charles River Japan Inc., 8-9 week-old in use) were anesthetized by subcutaneous administration of urethane (1.2 g/kg). After incision of cervical median, jugular catheter for administration of drug and arterial catheter for measurement of blood pressure were inserted. After incising of hypogastrium median, urethra was tied off in the vicinity of pubic bone. Urethra catheter was inserted into urethra by incision of dome of urinary bladder and fixed by ligation at the bladder neck. Urethra catheter was connected to the pressure tranducer and urethral pressure was measured. Subsequently, urethral pressure was adjusted about 20 mmHg and left until stabilizing (for about 20 minutes). The highly active LPA prepared in Example 1, Example 1-1 or Example 1-2, or LPA, which is material for preparation thereof, was administrated intravenously and the action of increasing urethral pressure was evaluated.

<Result≦

As a result of comparing activity between LPA and highly active LPA using the increasing urethral pressure measuring system under anesthesia of rat with urethane, the highly active LPA increased urethral pressure more strongly than LPA. For example, as a result of comparing activity between 1-linolenoyl(18:3)-LPA obtained in Reference Example 1 and highly active LPA obtained in Example 1, highly active LPA induced at least 1.5- to 2-fold increase of urethra pressure than 1-linolenoyl(18:3)-LPA at the dose of 0.3 mg/kg, i.v. . And also, as a result of comparing activity between 1-linoleoyl(18:2)-LPA and highly active LPA obtained in Example 1-1,1-linoleoyl(18:2)-LPA increased urethral pressure to 0.6 mmHg, highly active LPA obtained in Example 1-1 increased urethral pressure to 5.4 mmHg correspondingly, at the dose of 0.3 mg/kg, i.v. . Moreover, 1-linoleoyl(18:2)-LPA increased urethral pressure to 0.8 mmHg, highly active LPA obtained in Example 1-1 increased urethral pressure to 8.5 mmHg correspondingly, at the dose of 1.0 mg/kg, i.v.

EXAMPLE 4

Preparation of Highly Active LPA from (2S)-2-hydroxy-3-[(9Z)-9 octadecenoyloxy]propyl Phosphate. Disodium Salt (Hereinafter, Referred to as oleoyl(18:1)-LPA

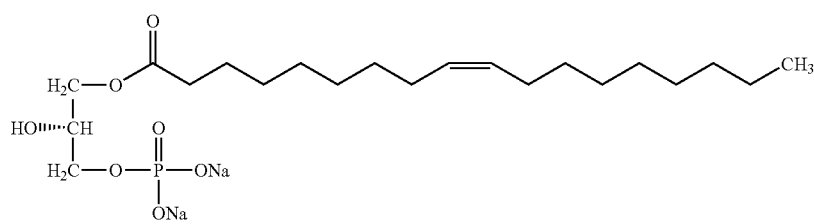

To a mixed solution of acetonitrile containing oleoyl (18:1)-LPA (Sigma, L-7260) (12.2 mg) and methanol (acetonitrile:methanol=1:2) (9.36 mL) was a mixed solution of acetonitrile containing metachloro perbenzoic acid (31.3 mg) and methanol (acetnitrile:methanol=1:2) (1.16 mL) and the solution was stirred. The solution was left at room temperature for 38 hours and concentrated. The obtained residue was dissolved in chloroform (0.6 mL) and purified by column chromatography on silica gel (Sep-Pak Vac Silica 6 cc (500 mg), chloroform:methanol=1:0-0:1) to give the highly active LPA, (2S)-2-hydroxy-3-[8-(3-octyl-2-oxiranyl)octanoyloxy]propyl phosphate disodium salt

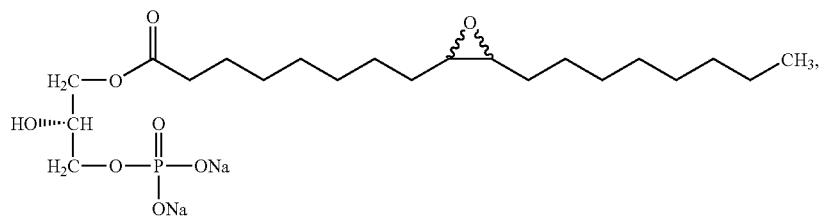

(2S)-2-hydroxy-3-(10-hydroxy-8-octadecenoyloxy)propyl phosphate disodium salt

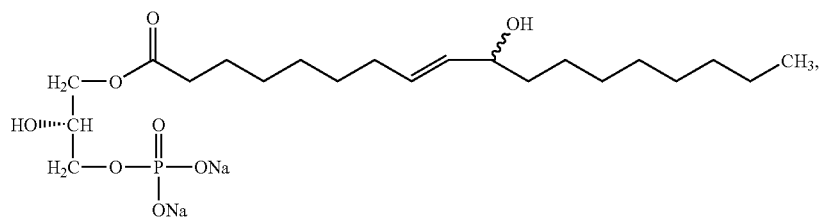

and/or (2S)-2-hydroxy-3-(9-hydroxy-10-octadecenoyloxy)propyl phosphate disodium salt

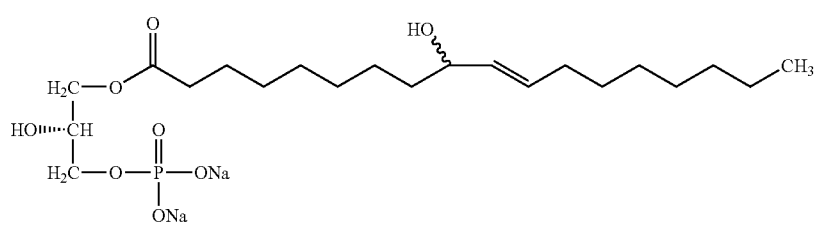

(11.3 mg) having the following physical data

<Mass Spectrum Data>

HRMS (Q-TOF-ESI Neg.) (m/z): (M−H)⁻ calcd for $C_{21}H_{40}O_8P$ 451.2461, found 451.2398; HRMSMS (Q-TOF-ESI Neg.) (m/z): [M−H]⁻—$C_3H_7O_5P$ 297.2430, [M−H]⁻—$C_3H_7O_5P$—$H_2O$ 279.2334, [M−H]⁻—$C_{18}H_{32}O_2$ 171.0090, [M−H]⁻—$C_{18}H_{32}O_2$—$H_2O$ 152.9979.

EXAMPLE 5

Preparation of Highly Active LPA from 1-linoleoyl(18:2)-LPA

To a solution of ammonium formate (1.8 mL, 10 mM, pH 9.0) containing D(+)-sn-1-O-linoleoyl-glyceryl-3-phosphate sodium salt (echeon, L-0182) (2.0 mg) was added a solution of ammonium formate (1.0 mL, 10 mM, pH 9.0) containing Soybean lipoxygenase (50000 U/mL). The solution was stirred and left at room temperature for 6 hours to give the highly active LPA, (2S)-2-hydroxy-3-(9-hydroperoxy-10,12-octadecadienoyloxy)propyl phosphate

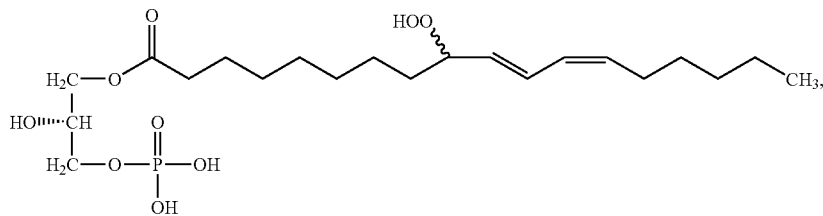

(2S)-2-hydroxy-3-(10-hydroperoxy-8,12-octadecadienoyloxy)propyl phosphate

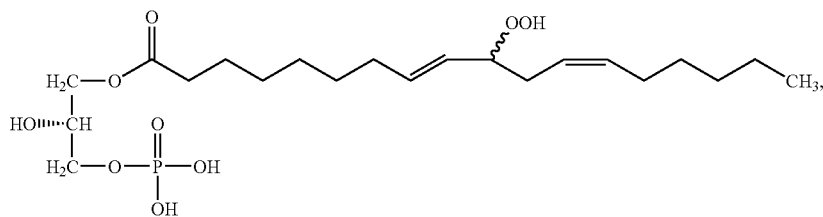

(2S)-2-hydroxy-3-(12-hydroperoxy-9,13-octadecadienoyloxy)propyl phosphate

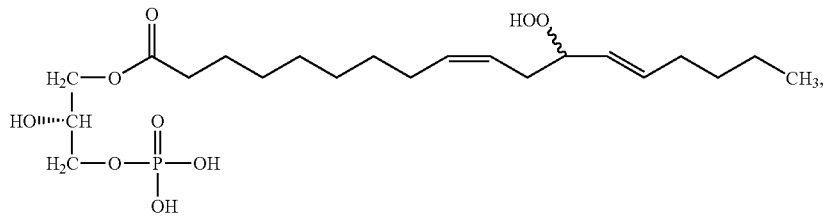

and/or (2S)-2-hydroxy-3-(13-hydroperoxy-9,11-octadecadienoyloxy)propyl phosphate

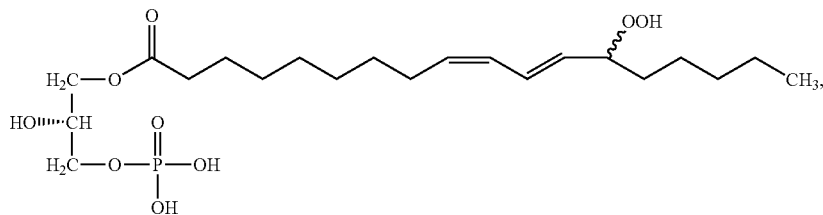

having the following physical data.

<Mass Spectrum Data>

HRMS (Q-Tof-ESI Neg.) (m/z): [M−H]⁻ calcd for $C_{21}H_{36}O_9P$ 463.2097, found 463.2090; HRMSMS (Q-Tof-ESI Neg.) (m/z): [M−H]⁻—$C_3H_7O_5P$—$H_2O$ 291.2151, [M−H]⁻—$C_{18}H_{30}O_3$ 171.0269, [M−H]⁻—$C_{18}H_{30}O_3$—$H_2O$ 153.0096.

EXAMPLE 5-1

Preparation of Highly Active LPA from 1-linolenoyl(18:3)-LPA

By the same procedure as described in Example 5, using D(+)-sn-1-O-linolenoyl-glyceryl-3-phosphate sodium salt (echeon, L-0183) instead of D(+)-sn-1-O-linoleoyl-glyceryl-3-phosphate sodium salt, the highly active LPA, (2S)-2-hydroxy-3-(9-hydroperoxy-10,12,15-octadec-atrienoyloxy)propyl phosphate

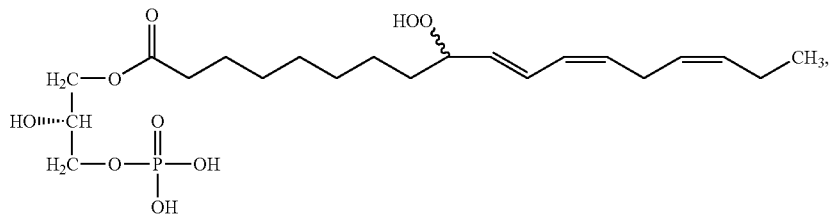

(2S)-2-hydroxy-3-(10-hydroperoxy-8,12,15-octadec-atrienoyloxy)propyl phosphate

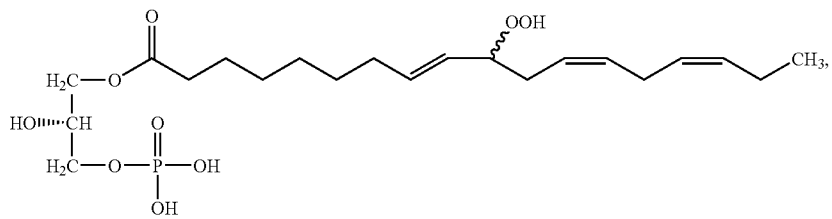

(2S)-2-hydroxy-3-(12-hydroperoxy-9,13,15-octadec-atrienoyloxy)propyl phosphate

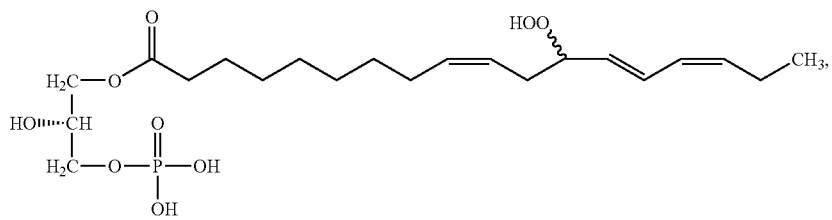

(2S)-2-hydroxy-3-(13-hydroperoxy-9,11,15-octadec-atrienoyloxy)propyl phosphate

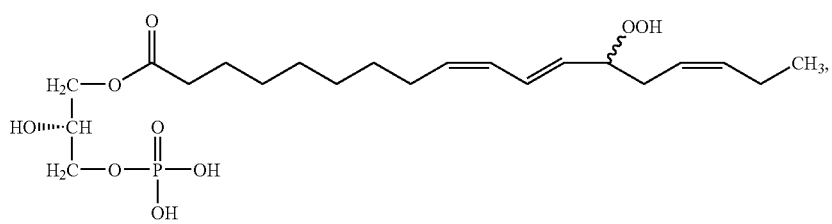

(2S)-2-hydroxy-3-(15-hydroperoxy-9,12,16-octadec-atrienoyloxy)propyl phosphate

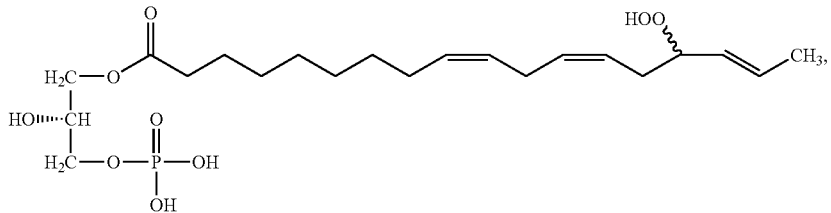

and/or (2S)-2-hydroxy-3-(16-hydroperoxy-9,12,14-octadec-atrienoyloxy)propyl phosphate

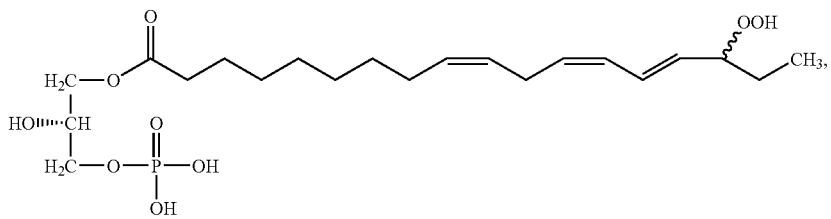

having the following physical data was obtained.

<Mass Spectrum Data>

HRMS (Q-Tof-ESI Neg.) (m/z): [M–H]⁻ calcd for $C_{21}H_{36}O_9P$ 463.2097, found 463.2090; HRMSMS (Q-Tof-ESI Neg.) (m/z): [M–H]⁻—$C_3H_7O_5P$—$H_2O$ 291.2151, [M–H]⁻—$C_{18}H_{30}O_3$ 171.0269, [M–H]⁻—$C_{18}H_{30}O_3$—$H_2O$ 153.0096.

EXAMPLE 6

Detection of Highly Active LPA in Plasma of Normal Animal (i) Blood Drawing

Normal rats (Crj:CD (SD) IGS (male, bought from Nippon Charles River) 10 weeks age in use) were fasted for 24 hours and collected blood with heparin from cervical vein using the positioner.

(ii) Preparation of Plasma

To a mixed solution of ethanol containing 50 μL of 2,6-di-t-butyl-4-hydroxytoluene (20 mg/mL) and 50 μL of saline containing ascorbic acid (2 mg/mL) in glass test tube was added 1.0 mL of the collected blood or saline. The mixture was stirred for 5 seconds and immediately, methanol (2.5 mL) and acetic acid (60 μL) were added thereto. The mixture was stirred 2 minutes and immediately, chloroform (1.25 mL) was added thereto. The mixture was stirred at room temperature for 1 minutes and left for 10 minutes. Moreover, chloroform (1.25 mL) was added thereto. The mixture was stirred at room temperature for 30 seconds. Brine (1.25 mL) was added thereto and the mixture was stirred for 1 minutes. The mixture was separated by centrifugation at 4° C. for 10 minutes. The chloroform layer was collected and chloroform (1.25 mL) was added to a water layer. The mixture was stirred for 1 minutes and separated by centrifugation at 4° C. for 10 minutes. The obtained chloroform layer was mixed in the above collected chloroform layer and the mixture was dried at room temperature for 80 minutes under nitrogen atmosphere. After drying, it was dissolved in 70% methanol (200 μL) containing sodium dihydrogen phosphate (100 mM) under nitrogen atmosphere. The mixture was separated by centrifugation for 5 minutes and a supernatant was collected a tube for analysis to give a sample for assay.

(iii) The Measurement by Mass Spectroscope

The sample for assay was measured by mass spectroscope. Hereinafter, condition for measuring and procedure are described.

<Material> silica gel column: Atlantis dC18, 3 μm (2.1 mm×50 mm) (Waters Co., Ltd.) pre column: Atlantis dC 18, 3 μm (2.1 mm×10 mm) (Waters Co., LTD)

<Prepared Reagent>

HPLC Elution Buffer (1) Buffer A: 10 mM ammonium formate (pH 6.4) aqueous solution
(2) Buffer B: 10 mM ammonium formate (pH 6.4)/methanol solution <Instrument>

(1) HPLC (Hewlett Packard, HP1100)
(2) tandem mass spectrometry (Micromass, Quattro micro API)

<Procedure>

Measurement was conducted by using above-mentioned apparatus with following conditions of HPLC and mass spectrometry ESI-MS Negative Ion Mode

[Sourse]

Polarity: ES–; Capillary (kV): 2.5; Extractor (V): 2; RF Lens (V): 0; Sourse Temp (° C.): 120; Desolvation Temp (° C.): 350; Cone Gas Flow (L/Hr): 59; Desolvation Gas Flow (L/Hr): 610

[MS]

LM1 Resolution: 15; HM1 Resolution: 15; Ion Energy1: 0.5; Entrance: −3; Exit: 1; LM2 Resolution: 15; HM2 Resolution: 15; Ion Energy2:3; Multiplier (V): 650; Syringe Pump Flow (µL/min): 10; Gas Cell Pirani Pressure (mbar): 2.86E-03

[MSMS]

Cycle time (secs): 1.760; Inter Channel delay (secs): 0.02; Retention window (mins): 0.000 to 35.000; Ionization mode: ES−; Data type: MRM data

|   | Chan Reaction | Dwell (secs) | Cone Volt. | Col Energy |
|---|---|---|---|---|
| 1 | 423.25 > 153.00 | 0.20 | 34.0 | 22.0 |
| 2 | 431.22 > 153.00 | 0.20 | 34.0 | 22.0 |
| 3 | 433.24 > 153.00 | 0.20 | 34.0 | 22.0 |
| 4 | 435.25 > 153.00 | 0.20 | 34.0 | 22.0 |
| 5 | 447.21 > 153.00 | 0.20 | 34.0 | 22.0 |
| 6 | 449.23 > 153.00 | 0.20 | 34.0 | 22.0 |
| 7 | 465.23 > 153.00 | 0.20 | 34.0 | 22.0 |
| 8 | 457.24 > 153.00 | 0.20 | 34.0 | 22.0 |
| 9 | 471.21 > 153.00 | 0.20 | 34.0 | 22.0 |
| 10 | 473.23 > 153.00 | 0.20 | 34.0 | 22.0 |
| 11 | 489.23 > 153.00 | 0.20 | 34.0 | 22.0 |

[LC]

HPLC Gradient: ratio (%) of Buffer A and Buffer B is shown in parentheses ( ). 0-1 min (70:30); 15 min (0:100); 30 min (0:100); 30.1 min (70:30); 35 min (70:30) Flow Rate: 0.2 mL/min Injection Vol.: 20 µL Column Temp (° C.): 25

<Result>

The peak area (Area Abs) in chromatography chart of ionized signal was calculated from the measured value with MassLynx analysis soft (Waters). The result was shown in the following table.

|   |   | (Area Abs) | |
|---|---|---|---|
|   | mz | blank | rat plasma |
| 17:0-LPA | 423.25 | 26 | 115 |
| 18:1-LPA | 435.25 | 168 | 3650 |
| 18:2-LPA | 433.24 | 673 | 75270 |
| 18:3-LPA | 431.22 | 28 | 848 |
| 20:4-LPA | 457.24 | 1380 | 85147 |
| 18:2-LPA, O-H2 | 447.21 | BQL | BQL |
| 18:2-LPA, O | 449.23 | 2 | 27 |
| 18:2-LPA, O2 | 485.23 | 18 | 13 |
| 20:4-LPA, O | 473.23 | BQL | 113 |
| 20:4-LPA, O-H2 | 471.21 | BQL | BQL |
| 20:4-LPA, O2 | 489.23 | BQL | BQL |

BQL: Below Quantify Limit

The oxidized compound was separated with non-oxidized compound specifically, and detected with a tandem mass spectrum device. For example, a compound that one oxygen atom attached to 20:4- LPA (m/z:473.23) was below quantification limit. On the one hand, The peak area was 113 in plasma of normal rat.

INDUSTRIAL APPLICABILITY

The present invention can be used in medical field as described below.

By the present invention, a preventive and/or therapeutic substance for diseases in which LPA takes part can be obtained effectively. The method of screening of the present invention is different from conventional method of using LPA, and is the method of screening which reflects in vivo environment by reason of using the highly active LPA which is a causative agent of various diseases as ligand. The substance obtained by the method of screening of the present invention is able to be useful as a medicament.

The invention claimed is:

1. A method of screening for a therapeutic substance, which comprises contacting an LPA receptor with an optionally labeled highly active LPA compound represented by formula (I), (II) or (III):

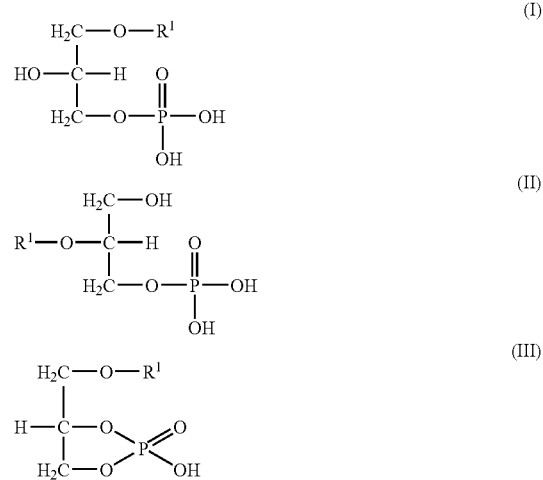

wherein $R^1$ represents

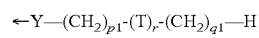

wherein arrowhead represents a binding site(s); Y represents carbonyl or methylene; p1 and q1 each independently represents an integer of 1 to 7; T represents

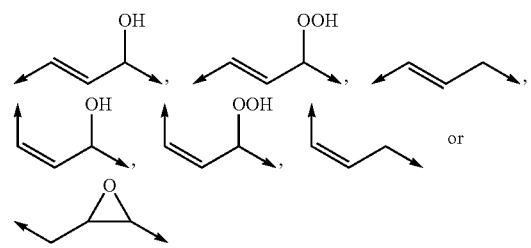

wherein arrowhead represents a binding site(s), and wherein asymmetric carbon means R-configuration, S-configuration or a mixture thereof in any ratio;

r represents an integer of 1 to 5 and when r represents 2 or more, plural r are the same or different, and wherein at least one of T in $R^1$ represents:

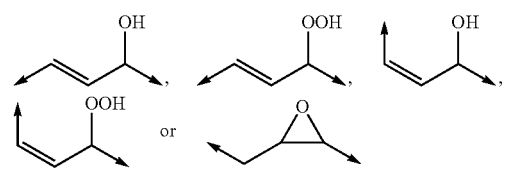

wherein arrowhead represents a binding site(s), and wherein asymmetric carbon means R-configuration, S-configuration or a mixture thereof in any ratio, a salt thereof.

2. The method according to claim 1, wherein R¹ represents a C18 aliphatic hydrocarbon-carbonyl group which contains 2 to 3 double bonds and is substituted with 1 hydroperoxy group.

3. The method according to claim 2, wherein R¹ represents:

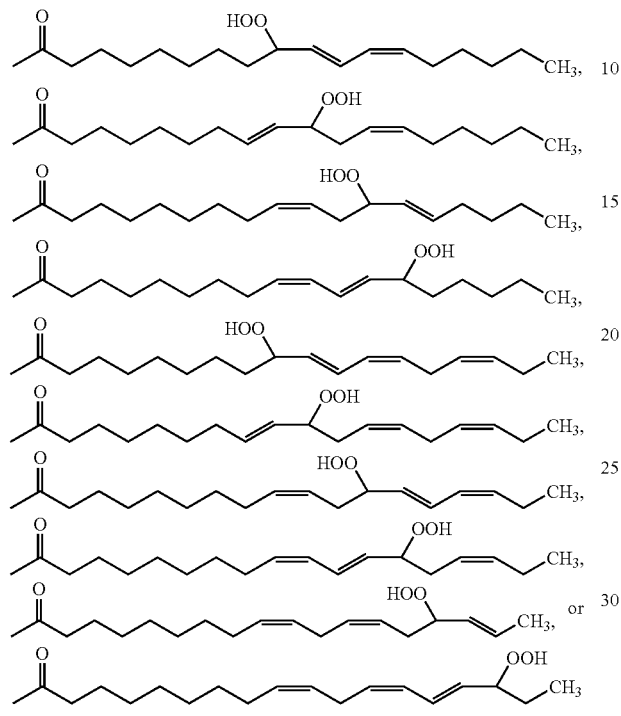

wherein asymmetric carbon means R-configuration, S-configuration or a mixture thereof in any ratio.

4. The method according to claim 1, wherein R¹ represents a C18 aliphatic hydrocarbon-carbonyl group which contains 0 or 1 to 2 double bond(s) and is substituted with 1 to 3 epoxy group(s).

5. The method according to claim 4, wherein R¹ represents:

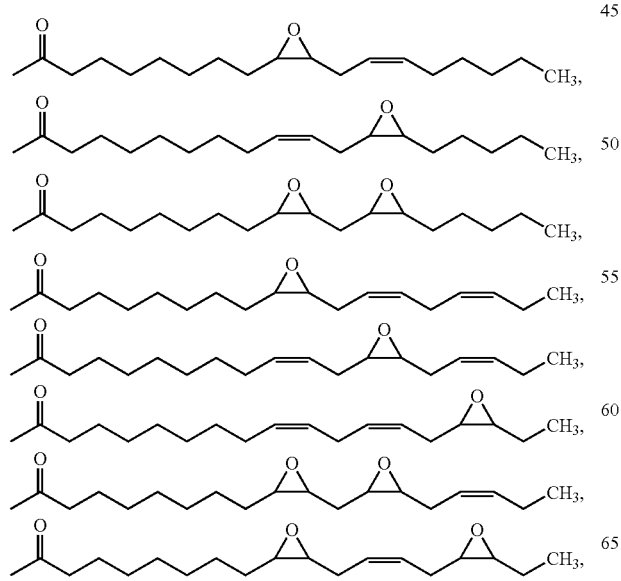

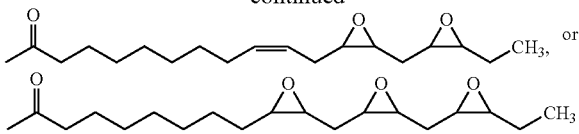

wherein asymmetric carbon means R-configuration, S-configuration or a mixture thereof in any ratio.

6. A screening kit, which comprises an optionally labelled highly active LPA is a compound represented by formula (I), (II) or (III):

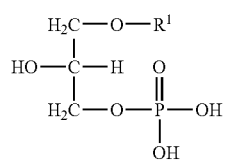

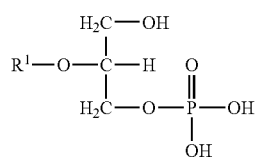

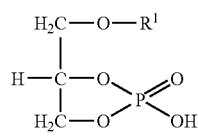

wherein R¹ represents

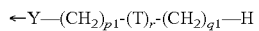

wherein arrowhead represents a binding site(s); Y represents carbonyl or methylene; p1 and q1 each independently represents an integer of 1 to 7; T represents

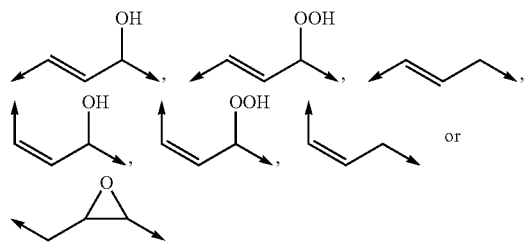

wherein arrowhead represents a binding site(s), and wherein asymmetric carbon means R-configuration, S-configuration or a mixture thereof in any ratio;

r represents an integer of 1 to 5 and when r represents 2 or more, plural r are the same or different, and wherein at least one of T in R¹ represents:

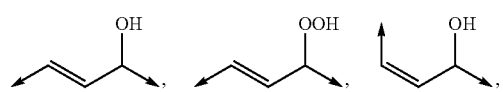

-continued

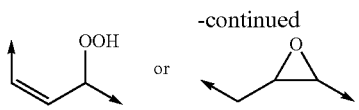

wherein arrowhead represents a binding site(s), and wherein asymmetric carbon means R-configuration, S-configuration or a mixture thereof in any ratio,
or a salt thereof.

7. The method according to claim 1, which comprises using both (1) the optionally labelled highly active LPA and (2) a LPA receptor protein, a partial peptide thereof, or a salt thereof.

8. The method according to claim 7, wherein the LPA receptor is EDG-2, EDG-4, EDG-7 or GPR23.

9. The method according to claim 7, which comprises comparing (1) the measured increase of intracellular concentration of calcium ion of the cell after contacting (a) the optionally labelled highly active LPA and (b) the cell which comprises the LPA receptor protein, to (2) the one after contacting (a) the optionally labelled highly active LPA, (b) the cell which comprises the LPA receptor protein and (c) the testing compound.

10. The method according to claim 7, which comprises comparing (1) the amount of the labelled highly active LPA which is bound to the LPA receptor protein, the partial peptide thereof, or the salt thereof after contacting (a) the labelled highly active LPA and (b) the LPA receptor protein, the partial peptide thereof, or the salt thereof, to (2) the one after contacting (a) the labelled highly active LPA, (b) the LPA receptor protein, the partial peptide thereof, or the salt thereof and (c) the testing compound.

11. The method according to claim 7, which comprises comparing (1) the amount of the labelled highly active LPA which is bound to the cell after contacting (a) the labelled highly active LPA and (b) the cell which comprises the LPA receptor protein, to (2) the one after contacting (a) the labelled highly active LPA, (b) the cell which comprises the LPA receptor protein and (c)the testing compound.

12. The method according to claim 7, which comprises comparing (1) the amount of the labelled highly active LPA which is bound to the membrane fraction of the cell after contacting (a) the labelled highly active LPA and (b) the membrane fraction of the cell which comprises the LPA receptor, to (2) the one after contacting (a) the labelled highly active LPA, (b) the membrane fraction of the cell which comprises the LPA receptor and (c) the testing compound.

13. A chemically or enzymatically synthesized compound represented by formula (I), (II) or (III):

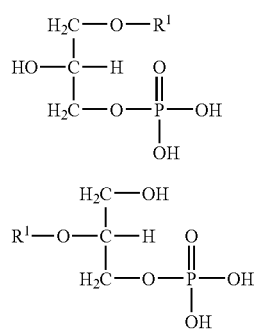

-continued

wherein $R^1$ represents $\leftarrow Y-(CH_2)_{p1}-(T)_r-(CH_2)_{q1}-H$ wherein arrowhead represents a binding site(s); Y represents carbonyl or methylene; p1 and q1 each independently represents an integer of 1 to 7; T represents

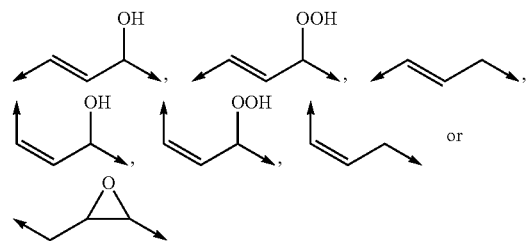

wherein arrowhead represents a binding site(s), and wherein asymmetric carbon means R-configuration, S-configuration or a mixture thereof in any ratio;
r represents an integer of 1 to 5 and when r represents 2 or more, plural r are the same or different, and
wherein at least one of T in $R^1$ represents:

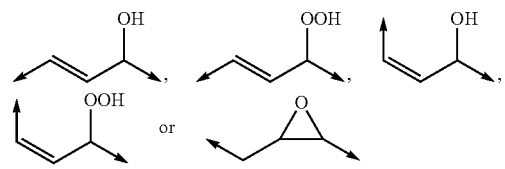

wherein arrowhead represents a binding site(s), and wherein asymmetric carbon means R-configuration, S-configuration or a mixture thereof in any ratio,
or a salt thereof.

14. The compound according to claim 13, wherein $R^1$ represents a C18 aliphatic hydrocarbon-carbonyl group which contains 2 to 3 double bonds and is substituted with 1 hydroperoxy group.

15. The compound according to claim 14, wherein $R^1$ represents:

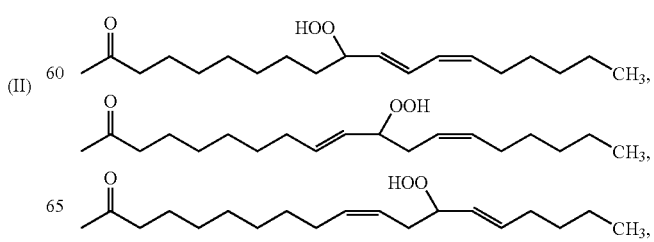

-continued

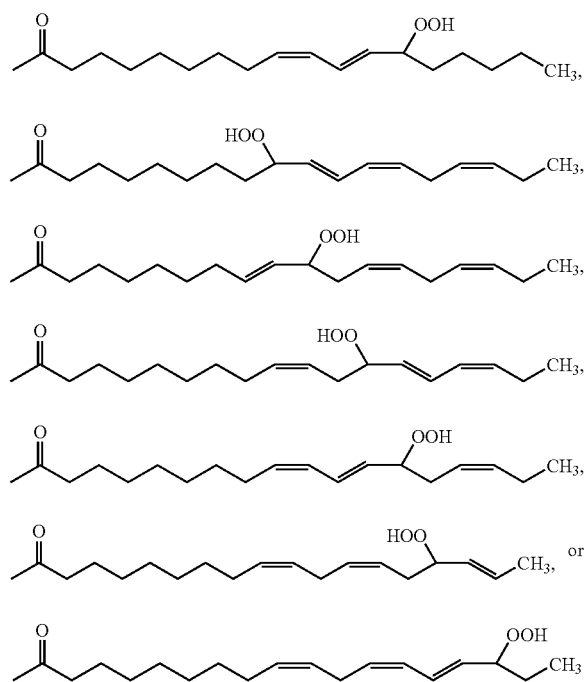

wherein asymmetric carbon means R-configuration, S-configuration or a mixture thereof in any ratio.

16. The compound according to claim 13, wherein $R^1$ represents a C18 aliphatic hydrocarbon-carbonyl group which contains 0 or 1 to 2 double bond(s) and is substituted with 1 to 3 epoxy group(s).

17. The compound according to claim 16, wherein $R^1$ represents:

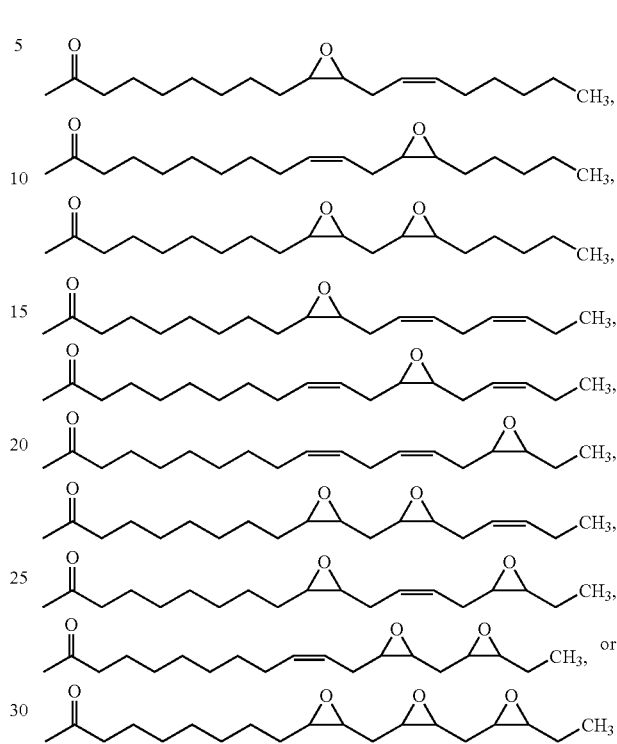

wherein asymmetric carbon means R-configuration, S-configuration or a mixture thereof in any ratio.

* * * * *